United States Patent [19]
Hamilton et al.

[11] Patent Number: 6,140,494
[45] Date of Patent: Oct. 31, 2000

[54] SQUARATE DYES AND THEIR USE IN FLUORESCENT SEQUENCING METHOD

[75] Inventors: Alan Lewis Hamilton, Amersham; Richard Martin West, Middlesex; William Jonathan Cummins, Herts; Mark Samuel Jonathan Briggs, Buckinghamshire, all of United Kingdom; Ian Edward Bruce, Dunslaughlin, Ireland

[73] Assignee: Amersham Pharmacia Biotech UK Limited, Buckinghamshire, United Kingdom

[21] Appl. No.: 09/171,303

[22] PCT Filed: Apr. 21, 1997

[86] PCT No.: PCT/GB97/01105
§ 371 Date: May 12, 1999
§ 102(e) Date: May 12, 1999

[87] PCT Pub. No.: WO97/40104
PCT Pub. Date: Oct. 30, 1997

[30] Foreign Application Priority Data

Apr. 19, 1996 [EP] European Pat. Off. .............. 96302783

[51] Int. Cl.[7] ..................................................... C07H 21/04
[52] U.S. Cl. .......................................... 536/26.6; 549/510
[58] Field of Search ................................ 536/26.6, 25.34; 568/839; 549/510

[56] References Cited

U.S. PATENT DOCUMENTS

| | | | |
|---|---|---|---|
| 4,830,786 | 5/1989 | Pease et al. | 260/396 N |
| 5,227,498 | 7/1993 | Lee et al. | 549/404 |
| 5,268,486 | 12/1993 | Waggoner et al. | 548/427 |
| 5,486,616 | 1/1996 | Waggoner et al. | 548/217 |
| 5,569,587 | 10/1996 | Waggoner | 435/6 |
| 5,569,766 | 10/1996 | Waggoner et al. | 548/150 |

FOREIGN PATENT DOCUMENTS

| | | |
|---|---|---|
| 0 214 847 | 3/1987 | European Pat. Off. . |
| 39 12 046 | 3/1990 | Germany . |
| WO 93/09172 | 5/1993 | WIPO . |
| WO 93/09956 | 5/1993 | WIPO . |

OTHER PUBLICATIONS

Mank et al., *Anal. Chem.*, 67: 1742–1748 (1995).

*Primary Examiner*—Scott W. Houtteman
*Attorney, Agent, or Firm*—Marshall, O'Toole, Gerstein, Murray & Borun

[57] ABSTRACT

Novel squarate dyes are described, and adducts of these dyes with biologically significant chemical species such as nucleosides or nucleotides. The adducts have useful properties for fluorescent nucleic acid sequencing methods.

12 Claims, No Drawings

SQUARATE DYES AND THEIR USE IN FLUORESCENT SEQUENCING METHOD

This invention concerns the use of a class of dyes in various biological applications. Some of the dyes are claimed as new compounds per se.

BACKGROUND TO THE INVENTION

The development of automated fluorescent methods has led to increased data generation in DNA sequencing projects. Smith et al U.S. Pat. No. 5,171,534 have described a fluorescent DNA sequencing system. Waggoner et al U.S. Pat. No. 5,268,486 have described the properties of some conjugates of cyanine dyes and Middendorf U.S. Pat. No. 5,230,781 and Patonay EP 670 374 have described the use of various cyanine dyes in DNA sequencing. Berger et al European patent 214 847 has described the use of other cyanine dyes some of which contain squarate groups in assays which involve a specific binding partner. Other squarate dyes are described by Pease et al in U.S. Pat. No. 4,830,786 and subsequent divisional patents, and by A J G Mank et al in Anal. Chem. 1995, 67, 1742–8. Cushman et al WO 93/09172 and Krutak et al WO94/19387 have described cyanine dyes containing squarate groups for use in thermoplastics and inks.

There is a need for methods of detecting biologically significant chemical species (hereafter biological molecules) at increased convenience and sensitivity in general and particularly for DNA sequencing and DNA mapping experiments.

SUMMARY OF PRESENT INVENTION

In one aspect the invention provides an adduct of any biological molecule with a squarate dye as defined below. Examples of biological molecules are peptides, proteins, antibodies, polysaccharides and drugs. Preferably the biological molecule is a nucleoside or nucleotide or analogue or oligonucleotide. An analogue of a nucleoside or nucleotide may be a nucleoside or nucleotide derivative or other sugar-heterocycle which inhibits or mimics biological activity of normal nucleosides or nucleotides towards nucleic acid modifying or polymerising enzymes. An example of a nucleotide analogue is a chain terminator, such as a dideoxynucleotide, as used in sequencing reactions. The adduct may have the formula Q—N—CO—Sq, where Q is a biological molecule such as a nucleoside or nucleotide or analogue or oligonucleotide residue, and Sq is a residue of a squarate dye, the two being joined by an amide linkage formed between an amine group of Q and a carboxylate group of Sq. Alternatively the linkage may be formed between a functional group such as carboxylic acid, or derivatives thereof, isothiocyanate, maleimide, iodoacetamide, or phosphoramidite, and a nucleophile such as an amine, thiol, hydroxy or other group, as known for other nucleotide or oligonucleotide adducts, whereby either the nucleophilic or electrophilic reactive grouping may be attached to the dye. Alternatively the dye containing O-alkyl or O-alkenyl or O-alkynyl on the central moiety but with no other reactive functional group on the rest of the molecule may react with an amine or thiol or alcohol group to form a covalent linkage to a biological molecule.

In a further aspect the invention provides for the labelling of species immobilised on solid supports. One example of this may be an immobilised labelled oligonucleotide monomer or a difunctional derivatised dye with one arm bound to a solid support which is used for automated DNA synthesis.

In a later step the labelled oligonucleotide is cleaved from the support. Another application may be the labelling of a suitably derivatised solid support which is used in a heterogeneous luminescence based assay. In this instance the label may or may not be cleaved from the support.

In another aspect, the invention provides an improved fluorescent sequencing method, which comprises using an adduct as defined.

Squarate dyes are described in EP 214 847, the disclosure of which is incorporated herein by reference. A major aspect of the present invention is concerned with a family of squarate dyes that are particularly suitable for use in the adducts and the improved fluorescent sequencing methods defined above. According to this aspect, the invention provides a squarate dye of the formulae (I), (II), (IIa), (III), (IV) or (IVa).

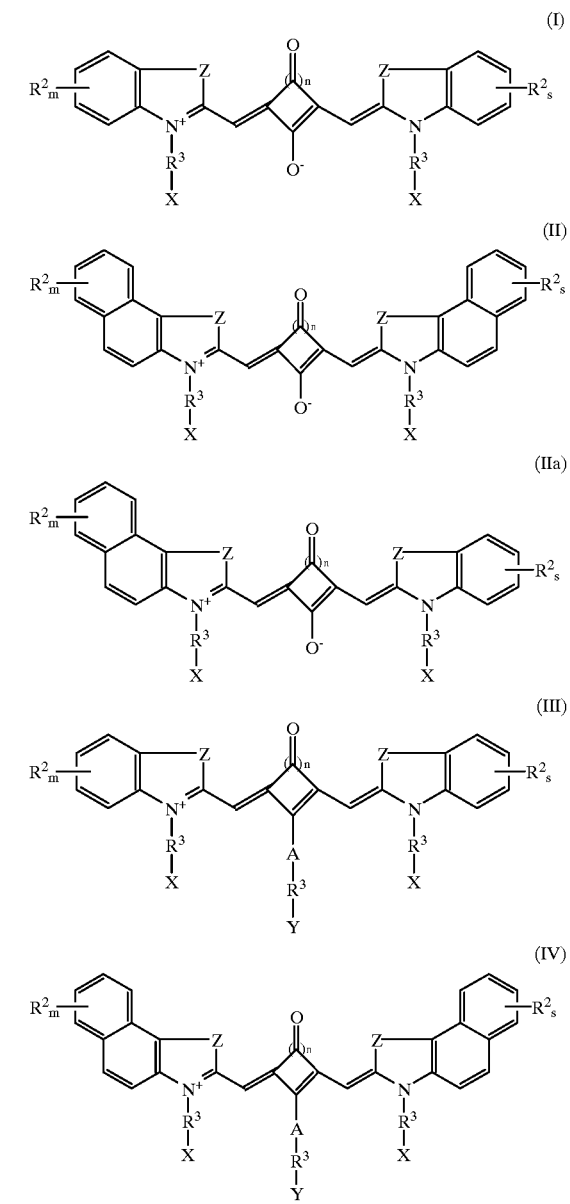

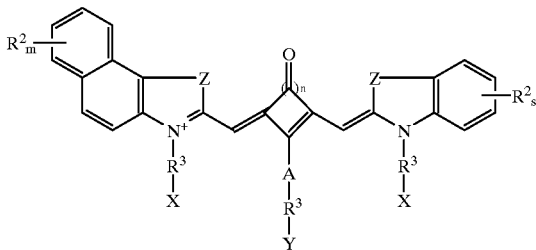

(IVa)

where
each Z is independently O or S or $CR^1_2$,
n=1–3,
$R^1$ is lower alkyl (1–4 carbon chain),
each $R^2$ is independently selected from electron donating and electron withdrawing groups such as halogen, alkoxy, primary secondary and tertiary amino, nitro, $SO_3^-$, and —$R^3$—X, or is a branched or straight chain of up to 30 carbon atoms incorporating one to five positively charged nitrogen atoms,
each $R^3$ is independently selected from: alkylene, alkenylene and alkynylene (1–20 carbon chain), or is a branched or straight chain of up to 30 carbon atoms incorporating one to five ether oxygen atoms or arylene rings or positively charged nitrogen atoms,
at least one X is a nucleophilic functional group, such as OH, SH or $NH_2$, or alternatively a grouping capable of reacting with a nucleophile, in which case X is preferably selected from the following:
$CO_2H$, activated carboxyl such as acid halide or anhydride, CO active ester, NCS, O phosphoramidite, $NC(O)CH_2l$ and

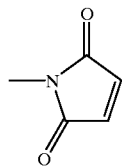

any other X present is independently selected from H and $SO_3^-$, and the residue of a squarate dye (whereby dimers and oligomers of the dyes shown as monomers of formula (I), (II), (IIa), (III), (IV) and (IVa) are envisaged) or other fluorochrome,
each of s and m is 0, 1 or 2,
A is O, $NR^4$ or S,
$R^4$ is alkyl, alkenyl, alkynyl or H, and
each Y is independently X or H.

At least one group $R^2$ may be $SO_3^-$ in the compounds of formula (I), (II) and (IIa). Except when X is phosphoramidite (when $SO_3^-$ groups are optional), preferably 1 to 5 $SO_3^-$ groups are present to provide improved solubility in aqueous solvents.

The presence of sulphonic acid groups within the dye confers several advantages, namely increased water solubility, increased photostability, brightness and the potential reduction of interactions with surroundings.

Biological molecules such as proteins, antibodies, DNA and RNA are intrinsically water soluble to enable them to carry out their functions in a biological environment. There are well known procedures for isolating them by the addition of organic solvents, such as ethanol, to precipitate them from solution. To enable them to be labelled by reactive dyes, the dye molecules themselves must be either soluble in an aqueous environment or a mixed aqueous organic environment that does not precipitate or denature the biological molecule being labelled. The presence of sulphonic acid groups on the described squarate dyes greatly enhances their water solubility. Thus the squarate dyes synthesised for comparative studies in Example 13 lacking the sulphonic acids were found to require the addition of dioxan for labelling a $H_2N$-DNA primer as described in Example 5. Although a degree of successful labelling of DNA could be achieved by such procedures the relatively high organic content would likely cause either precipitation or denaturing of a protein. The squarate dye (13c) in Example 13 derived from benzindole derivatives was initially found to be non-fluorescent. The fluorescent properties were restored by boiling the dye in a 1% SDS detergent solution to prevent aggregation and hence self-quenching of fluorescence. Such aggregation is well known for cyanine dyes in the photographic industry (West, W and Pierce S. J. Phys Chem 69, 1894 (1965), Sturmer, D M, Spec Top in Heterocyclic Chemistry, 30 (1974)). When the corresponding sulphonated dye (2h) in Example 2 was studied no such problems were encountered.

The presence of sulphonate groups on the squarate dye confers to the dye an overall net negative charge. This assists in reducing non-specific hydrophobic interaction with biological molecules. DNA and RNA are by nature negatively charged due to the phosphate backbone, thus a negatively charged dye will be repelled by electrostatic interactions and limit any labelling to the specific reaction of the attached reactive groups/nucleophile. Even after labelling the presence of sulphonate groups on the dye in the dye conjugate will assist in minimising hydrophobic interactions with any plastic components encountered in the manipulation of the squarate dye conjugate. In sequencing applications, particularly capillary gel sequencing, the negative charge on the dye will prevent any adverse interaction with the capillary wall coating within the capillary that would greatly distort the results, as the capillary wall coating has already been optimised for the negatively charged DNA.

The presence of a sulphonic acid group on the aryl portion of the dye imparts greater photostability to the dye. This is illustrated by the tables in Example 13, which has determined the $t_{1/2}$ of the dyes when exposed to a bright light source. All those squarate dyes lacking an aryl sulphonate have the lowest $t_{1/2}$. The presence of two sulphonic groups increases further the photostability. For comparison a commercially available cyanine dye (Cy5™) has also been included in the tables.

When the reactive group is a phosphoramidite the absence of a sulphonic acid group is preferred but not essential. It is well known that DNA/RNA can be synthesised on a solid support by using phosphoramidite nucleotide monomer building blocks. There is also a range of phosphoramidite labels that can be used to attach haptens and dyes within a growing DNA chain or at the terminal 5' or 3' end dependent upon the users requirements. S. L. Beaucage et al in Tetrahedron 49, 1925, (1993). Common to all these approaches is a protection strategy to ensure all reactive nucleophilic hydroxyl or amino functionalities within any phosphoramidite are protected to prevent reaction with the phosphorus (III) reagent during phosphoramidite activation and addition. On a DNA synthesiser these phosphoramidite additions are normally carried out in organic solvent, typically acetonitrile.

It has been found that alcohol derivatives of the squarate dyes of this invention can be readily converted to the required phosphoramidite derivative without recourse to protection of the hydroxyl species on the central cyclobutenediylium-1,3-diolate ring to which the indoleninium etc. intermediates have been coupled. This is an unexpected result and contrasts with the elaborate synthesis required to produce a fluorescein dye phosphoramidite performed by P. Theisen et al Tetrahedron Lett. 33, 5033, (1992). The absence of a sulphonic acid group in the squarate dye phosphoramidites is desirable so that acetonitrile can still be used as the reaction solvent of choice on the DNA synthesisers. It has also be found that phosphoramidites of the squarate dyes can be synthesised even when a sulphonic acid group is present. Both types of derivatives have been used to label a DNA primer and subsequently generate sequence information—see Example 11.

The synthesis of the squarate dyes can be carried out either in a one step procedure or by the reaction of squaric acid or its derivatives with first one chosen intermediate and isolation of the "half dye" type structure with subsequent reaction with the intermediate of choice to provide the required unsymmetrical dye. Example 1 provides a range of intermediates that can be used to prepare any specific dye of choice. Substituents ($R^2$) on the aromatic rings can lead to significant effects on the properties of the dyes, e.g. wavelength shifts and stability. (See The Chemistry of Synthetic Dyes, Venkataraman, Academic Press New York 1971, vol.4, chapter 5, part iiic, pages 228–240, particularly Table 1 on page 230.). The intermediates also provide a range of X derivatives that can be chosen e.g. OH, $NH_2$ which can both be readily converted into phosphoramidite or iodoacetamide respectively and carboxylic acid groups for conversion to activated carboxylic derivatives upon the required strategy for coupling to a biology molecule. Thus nucleotides such as 5'- aminoallyl dUTP require a succinimidyl ester squarate derivative where as a cysteine residue on a protein requires a maleimide or iodoacetimide squarate dye derivative. Those skilled in the art of conjugation will realise the conjugation strategies above are illustrative and are not meant to be limiting.

The variations induced by the variants in the substituents on the aromatic rings ($R^2$), or an increase in the number of conjugated aromatic rings (e.g. benzindole instead of indole) generally provide relatively subtle changes of wavelength and stability. A more significant change in wavelength properties can be induced by varying n in the central ring of the dye. These dyes are based on the squaric acid (n=1), croconic (n=2), and rhodizonic (n=3), collectively termed squarate dyes herein for brevity. The value of n determines the approximate maximum excitation wavelength: 570–690 nm n=1, 690–790 nm n=2, 790–890 nm n=3.

The synthesis of unsymmetrical squarate dyes with functional groups or reactive groups attached to linker arms either on the aromatic ring as an substituent or off the nitrogen in the heteroaromatic ring is an achievable process as demonstrated in the examples. Generally taking advantage of symmetry can improve the overall synthetic yields in any given process. The modification on the central cyclobutenediylium-1,3-diolate ring where n=1 and the corresponding derivatives where n=2 or 3 can provide an overall more efficient process as well as a novel labelling position. The Examples 7–10 provide processes wherein the squarate dyes are first converted to an ether derivative and then subsequently further reacted to provide the required functionality for attachment to a biological molecule. The modification of the initial ether derivatives is not necessarily required for attachment to biological molecules as the ether derivative itself will react with amine groups. Modification of the central ring is not the only strategy that can be employed to increase ease of synthesis. The monoprotection of difunctional squarate dyes (e.g. two identical X groups present ) as in Examples 11h and 11k can also provide mono-reactive derivatives. This approach also allows for deprotection of the second functional group for the subsequent reaction to a second biological molecule, stationary phase or dye as required.

The modification of the central ring has also been found to alter the fluorescent properties of the dyes. Thus, the replacement of the initial O methyl substituent with a $R^4$NMe group has been found to dramatically reduce fluorescence providing for a quencher type dye. When the substituent on the aromatic portion of the dye ($R^2$) is a nitro group the same sort of affect can be achieved.

These squarate dyes can be used in fluorescence energy transfer (ET). This technology is mediated by a dipole-dipole coupling between chromophores that results in resonance transfer of excitation from an excited donor chromophore to an acceptor chromophore (Forster, T (1965) in Modem Quantum Chemistry, Istanbul lectures, part III Ed. Sinanoglur, O (Academic, New York) pp 93–137).

Fluorescence ET is a useful spectroscopic phenomenon that is well known in biological analysis, (Stryer, L, Ann. Rev. Biochem., (1978) 47 819–846; Cardullo, R A, et al Proc. Natl. Acad. Sci USA, (1988) 85 8790–8794; Ozak H et al, Nucleic Acids Res., (1992) 20, 5205–5214; Clegg R M et al, Biochemistry (1992) 31 4846–4856 and Proc. Natl. Acad. Sci. USA, (1993) 90 p2994–2998; Selvin P R, Proc. Natl. Acad. Sci USA, (1994) 91 10024–10028).

In one example, the donor dye, absorbs light at the wavelength of, for example, the appropriate laser. The energy emitted from this donor dye is transferred to a second dye, the acceptor dye. This acceptor dye emits the energy as fluorescence at the normal wavelength at which the acceptor dye emits. For example, a system based upon squarate dyes derived from two indolinium intermediates, as a donor absorbing at ca. 633 nm, and an acceptor derived from benzindolinium intermediates, absorbing at ca. 665 nm, can be envisaged.

This principle has been used in many biological assays included DNA sequencing and analysis (Jingyue Ju et al Proc. Natl. Acad. Sci USA (1995) 92 p4347–4351).

In a further example the acceptor molecule may be chosen such that it quenches the energy emitted from the donor. The acceptor is then called a quencher. Such principles have been used in homogeneous gene detection assays. (Tyagi S et al Nature Biotechnology (1996) 14 (3) p303–308). Squarate dyes can be designed which can be used as donors and/or acceptors or quenchers as described above.

Thus the invention also provides a fluorescent labelling complex comprising:

a first or donor fluorochrome having first absorption and emission spectra;

a second or acceptor fluorochrome having second absorption and emission spectra, the wavelength of the emission maximum of said second fluorochrome being longer than the wavelength of the emission maximum of said first fluorochrome, and a portion of the absorption spectrum of said second fluorochrome overlapping a portion of the emission spectrum of said first fluorochrome;

at least one linker for covalently attaching said first and second fluorochromes for transfer of resonance energy transfer between said first and second fluorochromes;

a target bonding group capable of forming a covalent bond with a target compound;

wherein at least one of the said first and second fluorochromes is a squarate dye.

As demonstrated in the experimental section below, squarate oligonucleotides conjugates can be used successfully in automated fluorescent DNA sequencing. In this application they can offer several potential advantages over other dyes which absorb at shorter and longer wavelengths:
1. The 632 nm red HeNe laser is significantly cheaper than the Argon ion, GaAlAs, YAG and 594 nm HeNe lasers used in other DNA sequencers.
2. The optics and filters are much simpler and cheaper than diffraction grating, fibre optic and scanning confocal microscope arrangements used by other sequencers.
3. The longer excitation wavelength makes the use of soda lime glass plates possible, avoiding more expensive low-fluorescence borosilicate glass.
4. The red laser causes less background fluorescence from gel and buffer components which in turn increases signal to noise levels and improves sensitivity.
5. The squarate dyes are more photostable than other dyes such as cyanines.
6. By the careful selection of dyes with differing spectral characteristics DNA could be sequenced within one track on a slab or capillary gel based sequencing instrument.
7. By the careful manipulation of the overall dye charge versus the degree of dye lipophilicity it is possible to synthesis either pairs or sets of dyes such that they have a matched gel mobility shift upon conjugation to DNA. This provides for the ease of user analysis of all the raw sequence data and reduces the reliance upon complex deconvolution algorithms and computer generated results.

The squarate dye may include a branched or straight chain of up to 30 atoms incorporating 1–5 positively charged nitrogen atoms. Preferably each positively charged nitrogen atom is provided by a quaternary ammonium group, an imidazole group or a pyridinium group.

The above illustrates how the squarate dyes can be modified by the addition of charged residues, for example the sulphonate grouping which provides for negatively charged dyes. In certain applications neutral or positively charged dyes are either necessary or advantageous. The addition of various numbers of quaternary nitrogen species to the dyes will provide overall positively charged dyes if no sulphonate groups are present or overall negatively, neutral or positively charged dyes if sulphonate groups are present. The above combined with the ability to vary the wavelength of any given dye by the choice of dye starting materials and/or squaric acid derivatives allows for the synthesis of matched dyes suitable for 2D gel applications as outlined in Waggoner et al. WO 96/33406.

EXPERIMENTAL EXAMPLES

EXAMPLE 1

Synthesis of intermediates for dye synthesis

The starting quaternised indolenines and related derivatives were prepared according to the methods of R. B. Mujumdar et al. Bioconjugate Chemistry, 1993, 4, 105, G. Patonay et al. J.Org. Chem. 1995, 60, 2391 and E. Barni et al. Heterocyclic Chem, 1985,22,1727. A representative example is included in each case.

Potassium 2,3,3-trimethylindolenine-5-sulphonate (1a)

To a 2 l three necked round bottomed flask equipped with a mechanical stirrer was added acetic acid (300 ml), 3-methyl-2-butanone (168 ml, 1.6 mol) and 4-hydrazinobenzene sulphonic acid (100 g, 0.53 mol). This was then heated under reflux for 3 h and then cooled, with stirring, overnight. The resulting pink precipitate was collected by filtration and then dried in vacuo at 60° C.

The crude product was converted to the title potassium salt by dissolution in methanol followed by addition of a saturated solution of KOH in iso-propyl alcohol. The precipitated yellow solid was collected by filtration and dried in vacuo at 60° C.

$\delta_H$ (270 MHz,$D_2O$) 7.15 (1H, s), 7.11 (1H, dd, J=7.0, 1.2 Hz), 6.52 (1H, d, J=7.0 Hz), 2.21 (3H, s), 1.38 (6H, s).

Potassium 1-(4-sulphonatobutyl)-2,3,3-trimethylindoleninium-5-sulphonate (1b)

The potassium salt (la) (11.0 g, 40 mmol) and 1,4-butane sultone (6.5 g, 48 mmol) were mixed together in 1,2-dichlorobenzene (50 ml) and then heated with stirring at 110° C. for 8 h. The mixture was then cooled overnight. The excess liquid was decanted off and the residue triturated with iso-propyl alcohol, filtered and dried in vacuo at 60° C. This was then HPLC purified (C-18, $H_2O$/MeOH).

$\delta_H$ (270 MHz;$D_2O$) 8.08 (1H, s), 7.96 (1H, dd, J=9.0, 1.2 Hz), 7.31(1H, d, J 9 Hz), 4.48 (2H, t, J 7.5 Hz), 2.23 (2H, t, J=7.5 Hz), 2.04 (3H, s), 1.95 (2H, m), 1.48 (6H, s), 1.35 (2H, m).

1-(5-Carboxypentyl)-2,3,3-trimethylindoleninium-5-sulphonate (1c)

Synthesised by an analogous method to (1b)

$\delta_H$ (270 MHz;$D_2O$) 8.10 (1H, s), 7.99 (1H, dd, J=9.0, 1.2 Hz), 7.29 (1H, d, J=9.0 Hz), 4.48 (2H, t, J=7.5 Hz), 2.29 (2H, t, J=7.4 Hz), 2.01 (2H, m), 1.61(6H, s), 1.32–1.60 (4H, m); (270 MHz;DMSO $d_6$) 8.03 (1H, s), 7.96 (1H, d, J=8.24 Hz), 7.84 (1H, d, J=8.24 Hz), 4.46 (2H, t, J=7.14 Hz), 2.86 (3H, s), 2.23 (2H, t, J=7.14 Hz), 1.84 (2H, m), 1.55 (6H, s), 1.41 (4H, m)

6-Bromo-3-oxahexanoic acid

To a stirred solution of glycolic acid (2.03 g, 26 mmol) and 1,3-dibromopropane (6.41 g, 32 mmol) in THF (50 ml) was added sodium hydride (1.56 g, 65 mmol). This was stirred at room temperature for 16 h. The reaction mixture was quenched with dilute HCl (1.0 M, 100 ml) and then extracted into chloroform (3×50 ml). This was then washed with brine, dried, filtered and evaporated to dryness in vacuo. The residue was purified by chromatography ($SiO_2$, $CHCl_3$/MeOH) to yield the title compound (2.91 g, 57%).

$\delta_H$ (270 MHz;$CDCl_3$) 3.95 (2H, s), 3.41 (2H, t, J=7.0 Hz), 3.25 (2H, t, J=7.0 Hz), 1.57 (2H, m).

1-(5-Carboxy-4-oxapentyl)-2,3,3-trimethylindoleninium-5-sulphonate (1d)

Synthesised by an analogous method to (1b) using 6-bromo-3-oxahexanoic acid $\delta_H$ ($D_2O$) 8.10 (1H, s), 7.99 (1H, dd, J=9.0, 1.2 Hz), 7.29 (1H, d, J=9.0 Hz), 4.48 (2H, t, J=7.5 Hz), 3.95 (2H, s), 3.25 (2H, t, J=7.0 Hz), 1.61(6H, s), 1.57 (2H, m).

1-Ethyl-2,3,3-trimethylindoleninium-5-sulphonate (1e)

Synthesised by an analogous method to (1b)

$\delta_H$ (270 MHz;DMSO $d_6$) 8.02 (1H, s), 7.94 (1H, d, J=8.24 Hz), 7.83 (1H, d, J=8.24 Hz), 4.48 (2H, q, J=7.14 Hz), 2.85(3H, s), 1.54 (6H, s), 1.44 (3H, t, J=7.14 Hz).

1-Butyl-2,3,3-trimethylindoleninium-5-sulphonate (1f)

Synthesised by an analogous method to (1b)

$\delta_H$ (270 MHz;$D_2O$) 0.85 (2H, t), 1.35 (2H, m), 1.50 (6H, s), 1.83 (2H, quin), 4.36 (2H, t), 7.80 (1H, m), 7.91 (1H, m) and 8.02(1H, app s).

1-Ethyl-2,3,3-trimethylindoleninium iodide (1g)

Synthesised by an analogous method to (1b)

$\delta_H$ (270 MHz;DMSO $d_6$) 7.97 (m, 1H), 7.84 (m, 1H), 7.63 (m, 2H), 4.49 (q, 2H, J=7.14 Hz), 2.85 (s, 3H), 1.54 (s, 6H), 1.45 (t, 3H, J=7.14 Hz).

1-(4-Sulphonatobutyl)-2,3,3-trimethylindoleninium-5-acetic acid (1h)

Synthesised by an analogous method to (1b)

$\delta_H$ (270 MHz;DMSO $d_6$) 1.52 (6H, s), 1.74 (2H,quin), 1.96 (2H, quin), 2.83 (3H, s), 3.44 (2H, br s), 3.74 (2H, s), 4.47 (2H, br t), 7.51 (1H, d), 7.70 (1H ,s) and 7.96 (1H, d).

1-(5-Carboxypentyl)-2,3,3-trimethylindoleninium bromide (1i)

Synthesised by an analogous method to (1b)

$\delta_H$ (270 MHz;DMSO-d$_6$) 7.89 (m, 1H), 7.86 (m, 1H), 7.63 (m, 2H), 4.47 (t, 2H; J=7.42 Hz), 2.86 (s, 3H), 2.24 (t, 2H; J=7.14 Hz), 1.83 (m, 2H), 1.55 (s, 6H), 1.46 (m, 4H).

1-Butyl-2,3,3-trimethylindoleninium-5-acetic acid iodide (1j)

Synthesised by an analogous method to (1b)

$\delta_H$ (270 MHz;CD$_3$OD) 1.05 (3H, t), 1.45–1.60 (2H, m), 1.85–2.05 (2H, m), 3.75 (2H, s), 4.50 (2H, t), 7.57 (1H, d), 7.70 (1H, s) and 7.80 (1H,d).

1-Ethyl-2,3,3-trimethylbenzindoleninium iodide (1k)

Synthesised by an analogous method to (1b)

$\delta_H$ (270 MHz;CDCl$_3$) 1.52 (3H, t), 1.78 (12H, s), 2.97 (3H, s), 4.64 (2H, q), 7.75(2H, quin) and 8.20–8.50 (4H, m).

1-(5-Carboxypentyl)-2,3,3-trimethylbenzindoleninium bromide (1l)

Synthesised by an analogous method to (1b)

$\delta_H$ (270 MHz;CDCl$_3$) 1.50–1.95 (4H, m), 1.85 (12H, s), 2.05 (2H, quin), 2.37 (2H, t), 4.65 (2H, t), 7.70 (1H, t), 7.80 (1H, t), 8.05 (1H, d), 8.17 (1H, d), 8.25 (1H, d) and 8.35 (1H, d).

5-Iodopentyl acetate

5-Chloropentyl acetate (26.5 g, 0.16 mol) was added to a solution of sodium iodide (45 g, 0.30 mol) in dry acetone (200 ml). The resulting pale yellow solution was heated at reflux for 65 h, during which time a white solid separated (sodium chloride). The final mixture was cooled to room temperature and filtered to remove the NaCl, which was washed with acetone and diethyl ether, then dried under vacuum at 50° C. Expected yield of NaCl=9.4 g; isolated yield=9.47 g (100%).

The filtrate and washings were combined and the solvent removed under reduced pressure; the residue was partitioned between water and diethyl ether. The ether layer was retained, washed with aqueous sodium thiosulphate solution and brine, then dried (Na$_2$SO$_4$), filtered and the solvent removed under reduced pressure, to give titled compound as a yellow-tinged liquid, 39 g (95%).

$\delta_H$ (270 MHz, CDCl$_3$) 1.50 (2H, m), 1.65 (2H, m), 1.85 (2H, m), 2.05 (3H, s, C$\underline{H}_3$—COO—), 3.18 (2H, t, I—C$\underline{H}_2$—), 4.06 (2H, t, —C$\underline{H}_2$—OAc).

1-(5-Acetoxypentyl)-2,3,3-trimethylindoleninium iodide (1m)

5-Iodopentyl acetate (3.84 g, 15 mmol) was added to freshly distilled 2,3,3-trimethylindolenine (2.39 g, 15 mmol); this mixture was then heated at 100° C. for 4 h under nitrogen atmosphere, to give a reddish gum. After cooling to room temperature this was triturated repeatedly with diethyl ether and dried under high vacuum to give a viscous reddish gum, 6.1 g (98%). This material was used directly, without further purification.

3-(5-Acetoxypentyl)-1,1,2-trimethylbenz(e)indoleninium iodide (1n)

5-Iodopentyl acetate (19.4 g, 78 mmol) was heated to 50° C., then 1,1,2-trimethyl-1H-benz(e)indole (16.2 g, 77 mmol) was added. This mixture was heated at 100° C. for 4.5 h before cooling to room temperature. The solidified melt was dissolved in 10% methanol/dichloromethane (100 ml), then diluted with diethyl ether (400 ml) to precipitate the product. After 30 mins stirring the pale green crystals were collected, washed with ether and dried to give (1n), 33.1 g (92%).

MS (MALDI-TOF): 339

$\delta_H$(300 MHz, CDCl$_3$) 1.55 (2H, m, —C$\underline{H}_2$—), 1.68 (2H, m, —C$\underline{H}_2$—), 1.83 (6H, s, indole CMe$_2$), 1.97 (3H, s, C$\underline{H}_3$—COO—), 2.0 (2H, m, —C$\underline{H}_2$—), 3.2 (3H, s, indole C$_2$—C$\underline{H}_3$), 4.02 (2H, t, indole N—C$\underline{H}_2$—), 4.78 (2H, t, —C$\underline{H}_2$—OAc), 7.6–7.7 5 (2H, m), 7.82 (1H, d), 8.03 (2H, m), 8.08 (1H, d).

N-(3-Bromopropyl)triethylammonium bromide 1,3-Dibromopropane (20.0 g, 100 mmol) and triethylamine (5.06 g, 50 mmol) were mixed in dry toluene (50 ml). This solution was heated at 100° C. under nitrogen atmosphere for 4 h, during which time a thick white solid precipitated. The mixture was then cooled and the solid collected by filtration, washed with toluene and ether and dried under vacuum at 50° C. to give the titled compound 5.0 g (36%).

$\delta_H$ (300 MHz, DMSO) broad peaks. 1.17 (9H, 3×N$^+$—CH$_2$—C$\underline{H}_3$), 2.15 (2H, BrCH$_2$C$\underline{H}_2$CH$_2$—), 3.26 (8H, 4×N$^+$—C$\underline{H}_2$), 3.62(2H, Br—C$\underline{H}_2$—).

1-((3-Triethylammonium)propyl)-2,3,3-trimethylindolium dibromide (1o)

Freshly distilled 2,3,3-trimethylindolenine (0.8 g, 5 mmol) and N-(3-bromopropyl)-triethylammonium bromide (1.52 g, 5 mmol) were mixed and placed under an argon atmosphere. The mixture was then heated at 140° C. for 1.5 h, giving a deep red viscous melt, which solidified to a glass on cooling. It was ground to a powder under diethyl ether; this was collected by filtration, triturated with boiling acetone and recrystallised from methanol/acetonitrile to give the title compound as a pale pink powder, 795 mg (34%).

$\delta_H$ (300 MHz, DMSO) 1.22 (9H, t, J 6.6 Hz, 3×N$^+$—CH$_2$—C$\underline{H}_3$), 1.55 (6H, s, indole C3Me$_2$), 2.21 (2H, m, —CH$_2$C$\underline{H}_2$CH$_2$—), 2.92 (3H, s, indole C2-Me), 3.27 (6H, q, J 6.6 Hz, 3×N$^+$—C$\underline{H}_2$—CH$_3$), 3.51 (2H, ~t, —C$\underline{H}_2$—NEt$_3$), 4.57 (2H, ~t, indole N$^+$—C$\underline{H}_2$—), 7.64 (2H, m), 7.86 (1H, d, J 6.5 Hz), 8.12 (1H, d, J 7.3 Hz).

1-((3-Triethylammonium)propyl)-2,3,3-trimethylbenzothiazolium dibromide (1p)

Synthesised by an analogous method to (1o)

Recrystallised from 1-butanol/acetone.

$\delta_H$ (300 MHz,D$_2$O) 1.15 (9H, t, 3×N$^+$—CH$_2$—C$\underline{H}_3$), 2.3 (2H, m, —CH$_2$C$\underline{H}_2$CH$_2$—), 3.25 (6H, q, 3×N$^+$—C$\underline{H}_2$—CH$_3$), 3.45 (2H, ~t, —C$\underline{H}_2$—NEt$_3$), 4.6 (2H, ~t, indole N$^+$—C$\underline{H}_2$—), 7.4 (1H, t), 7.6 (1H, t), 8.0 (1H, d,), 8.1 (1H, d).

3-(3-Aminopropyl)-1,1,2-trimethylbenz(e)indolium bromide.HBr (1q)

Prepared according to Patonay et al., *J. Org. Chem.*, (1995), 60, 2391.

$\delta_H$ (300 MHz, DMSO) 1.77 (6H, s, indole C1Me$_2$), 2.24 (2H, m, —CH$_2$—C$\underline{H}_2$—CH$_2$—), 2.98 (3H, s, C2 C$\underline{H}_3$), 3.10 (2H, app q, —C$\underline{H}_2$—NH$_3^+$), 4.72 (2H, t, J 7.0 Hz, indole N—C$\underline{H}_2$—), 7.70–7.81 (2H, m)+8.21–8.39 (4H, m)=6× benzoindole aryl-H, 8.03 (3H, broad s, —N$\underline{H}_3^+$).

3-(3-N-Phthalimidopropyl)-1,1,2-trimethylbenz(e)indolium bromide. (1r)

Synthesised by an analogous method to (1q)

$\delta_H$ (300 MHz,CDCl$_3$) 1.84 (6H, s, indole C1Me$_2$), 2.44 (2H, m, —CH$_2$—C$\underline{H}_2$—CH$_2$—), 3.24 (3H, s, C2 C$\underline{H}_3$), 3.86 (2H, t, J 7.1 Hz, —C$\underline{H}_2$—phthalimide), 4.99 (2H, t, J 7.2 Hz, indole N—C$\underline{H}_2$—), 7.58–7.76 (7H, m), 7.94–8.02 (3H, m).

N-Ethyl-2-methylbenzothiazolium iodide (1s)

Synthesised by an analogous method to (1b)

$\delta_H$ (270 MHz, CDCl$_3$) 1.6 (6H, t, benzothiazole N—CH$_2$—C$\underline{H}_3$), 3.5 (3H, s, benzothiazole C2-C$\underline{H}$3), 5.0 (2H, q, benzothiazole N—C$\underline{H}$2—CH$_3$), 7.75 (1H, t)+7.85 (1H, t)+8.1 (1H, d)+8.3 (1H, d)=4×benzothiazole aryl-H. $\delta_H$ (270 MHz; CD$_3$OD) 1.60 (3H, t, NCH$_2$C$\underline{H}_3$), 3.23 (3H, s, Me), 4.86 (2H, q, NC$\underline{H}_2$CH$_3$), 7.82 (1H, t, ArH), 7.95 (1H, t, ArH), 8.28 and 8.32 (each 1H, overlapping d, ArH).

N-(5-Carboxypentyl)-2-methylbenzothiazolium bromide (1t)

Synthesised by an analogous method to (1b)

$\delta_H$ (270 MHz; CD$_3$OD) 1.57, 1.71 and 2.00 (each 2H, m), 2.26 (2H, t, CH$_2$CO$_2$H), 4.77 (2H, t, NCH$_2$), 7.82 and 7.93 (each 1H, t, ArH) and 8.21–8.40 (2H, m, ArH).

3-Ethyl-1,1,2-trimethylbenz(e)indoleninium-7-sulphonate (1u)

Synthesised by an analogous method to (1b)

$\delta_H$ (300 MHz; D$_2$O) 1.45 (3H,t, CH$_2$CH$_3$), 1.57 (6H, s, CMe$_2$), 4.46 (2H, q, CH$_2$CH$_3$), 7.79, 7.84, 8.04 and 8.18 (each 1H, d, ArH) and 8.26 (1H, d, ArH).

1-(5-Carboxypentyl)-1,1,2-trimethylbenz(e)indoleninium-7-sulphonate

Synthesised by an analogous method to (1b) to give insoluble grey powder which was used directly with structural confirmation obtained from product dyes.

3-Ethyl-6.8-disulphonato-1,1,2-trimethylbenz(e)indolium tosylate (1w)

Synthesised by an analogous method to (1b)

$\delta_H$ (300 MHz, D$_2$O) 1.39 (3H, app t, indole N—CH$_2$—CH$_3$), 1.53 (6H, s, indole C2Me$_2$), 2.18 (3H, s, tosylate —CH$_3$), 4.40 (2H, q, J 7.5 Hz, indole N—CH$_2$—CH$_3$), 7.15+7.50 (each 2H, ≈d, 4×tosylate aryl-H), 7.92 (1H, d, J 9.5 Hz), 8.42 (1H, s), 8.49 (1H, s), 8.79 (1H, d, J 9.5 Hz).

3-(5-Carboxypentyl)-6,8-disulphonato-1,1,2-trimethylbenz(e)indolium bromide (1x)

Synthesised by an analogous method to (1b)

$\delta_H$ (300 MHz, D$_2$O) 1.30 (2H, m), 1.48 (2H, m), 1.59 (6H, s, indole C2Me$_2$), 1.83 (2H, m), 2.19 (2H, t, J 7.2 Hz, —CH$_2$—CO$_2$H), 4.41 (2H, t, J 7.5 Hz, indole N—CH$_2$—), 7.92 (1H, d, J 9.5 Hz), 8.40 (1H, s), 8.53 (1H, s), 8.79 (1H, d, J 9.5 Hz).

1-Benzyl-2,3,3-trimethylindoleninium-5-sulphonate (1y)

Synthesised by an analogous method to (1b)

$\delta_H$ (300 MHz, CD$_3$OD) 1.66 (6H, s, CMe$_2$), 5.85 (2H, s, PhCH$_2$), 7.37–7.44 (5H, m, PhCH$_2$), 7.77 (each 1H, d, J 8.4, 4-CH), 7.91 (1H, dd, J 1.5 and 8.4, 6-CH) and 8.11 (1H, d, J 1.5, 7-CH).

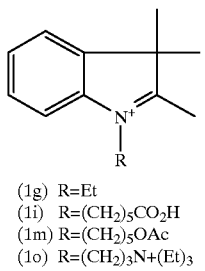

(1g) R=Et
(1i) R=(CH$_2$)$_5$CO$_2$H
(1m) R=(CH$_2$)$_5$OAc
(1o) R=(CH$_2$)$_3$N+(Et)$_3$

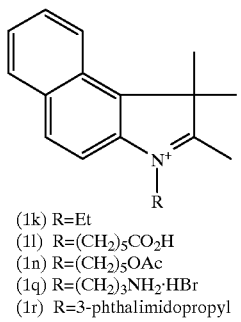

(1k) R=Et
(1l) R=(CH$_2$)$_5$CO$_2$H
(1n) R=(CH$_2$)$_5$OAc
(1q) R=(CH$_2$)$_3$NH$_2$·HBr
(1r) R=3-phthalimidopropyl

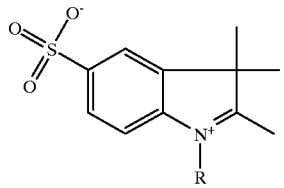

(1b) R=(CH$_2$)$_4$SO$_3$-
(1c) R=(CH$_2$)$_5$CO$_2$H
(1d) R=(CH$_2$)$_3$OCH$_2$CO$_2$H
(1e) R=Et
(1f) R=Bu
(1y) R=Bn

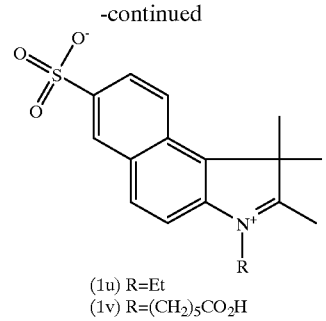

(1u) R=Et
(1v) R=(CH$_2$)$_5$CO$_2$H

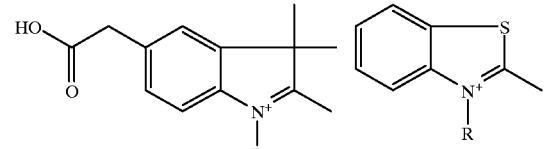

(1h) R=(CH$_2$)$_4$SO$_3$-
(1j) R=Bu (1p) R=(CH$_2$)$_3$N$^+$(Et)$_3$
(1s) R=Et
(1t) R=(CH$_2$)$_5$CO$_2$H

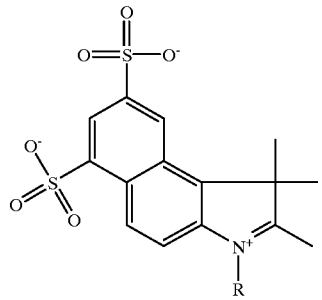

(1w) R=Et
(1x) R=(CH$_2$)$_5$CO$_2$H

EXAMPLE 2

Synthesis of sulphonic acid substituted squarate dyes from indoleninium intermediates For the invention dyes the exact nature of the counter-ions was not determined.

2-(1-(5-Carboxypentyl)-3,3-dimethyl-5-sulphonato-2-indolinylidenemethyl)-4-(1-(4-sulphonatobutyl)-3,3-dimethyl-5-sulphonato-2-indolinylidenemethyl)cyclobutenediylium-1,3-diolate (2a)

A mixture of (1b) (0.56 g, 1.35 mmol) and squaric acid (0.48 g, 4.05 mmol) in 2-ethoxyethanol (10 ml) was heated under reflux for 20 h. The reaction mixture was then evaporated to dryness in vacuo and purified by HPLC (C-18, H$_2$O/MeOH) to furnish an intermediate mono-adduct of squaric acid ($\lambda_{max}$(H$_2$O)=425 nm). Said adduct (0.27 g, 0.65 mmol) and (1c) (0.19 g, 0.71 mmol) in 2-ethoxyethanol (10 ml) were heated under reflux for 16 h. The 2-ethoxyethanol was removed in vacuo and the residue was purified by HPLC (C-18, H$_2$O/MeOH) to afford the title compound (2a).

$\delta_H$ (270 MHz;D$_2$O) 7.81 (2H, s), 7.65 (2H, d, J=7.5 Hz), 7.31–7.43 (2H, m), 6.27 (2H, m), 4.11 (4H, m), 2.89 (2H, t, J=7.0 Hz), 2.45 (2H, t, J=7.0 Hz), 1.4–2.0 (22H, m); $\lambda_{max}$ (H$_2$O)=631 nm.

2-(1-(5-Carboxypentyl)-3,3-dimethyl-5-sulphonato-2-indolinylidenemethyl)-4-(1-ethyl-3,3-dimethyl-5-sulphonato-2-indolinylidenemethyl)cyclobutenediylium-1,3-diolate (2b)

Squaric acid (121 mg, 1.06 mmol) in n-butanol (50 ml) was heated at reflux until all the squaric acid had dissolved. Then (1c) (500 mg, 1.06 mmol) was added portionwise over 2 h and the mixture was maintained at reflux for a further 2 h. 1-Ethyl-2,3,3-trimethylindoleninium-5-sulphonate (1e) (439 mg, 1.06 mmol) was added portionwise over 1 h. After heating at reflux for a further 24 h the mixture was cooled to ambient temperature and concentrated in vacuo. Purification of the residue by HPLC (C18, $H_2O$/MeOH) afforded the title compound as its n-butyl ester.

$\lambda_{max}$(MeOH) 636 nm; $\lambda_{em}$(MeOH) 652 nm $\delta_H$ (270 MHz;$CD_3OD$) 0.92 (3H, t, J=7.3 Hz), 1.38–1.93 (13H, m), 1.78 (12H, s), 2.34 82H, t, J=7.1 Hz), 4.04 (2H, t, J=6.6 Hz), 4.08–4.28 (4H, m), 6.02 (1H, s), 6.04 (1H, s), 7.25–7.35 (2H, m) and 7.82–7.92 (4H, m).

To a solution of the above dye butyl ester (13 mg) in water (2 ml) was added 1M KOH solution (0.5 ml). After stirring at ambient temperature overnight HPLC purification of the mixture (PRP-1, $H_2O$/MeOH) afforded the title compound as the potassium salt.

$\lambda_{max}$(MeOH) 636 nm; $\lambda_{em}$(MeOH) 647 nm $\delta_H$ (270 MHz;$CD_3OD$) 1.40 (3H, t, J=7.1 Hz), 1.45–1.58 (2H, m), 1.63–1.93 (4H, m), 1.78 (12H, s), 2.19 (2H, t, J=7.4 Hz), 4.09–4.28 (4H, m), 6.03 (1H,s), 6.04 (1H, s), 7.25–7.36 (2H,m) and 7.85–7.92 (4H, m)

2-(1-(5-Carboxypentyl)-3,3-dimethyl-5-sulphonato-2-indolinylidenemethyl)-4-(1-butyl-3,3-dimethyl-5-sulphonato-2-indolinylidenemethyl)cyclobutenediylium-1,3-diolate (2c)

The title compound was prepared as its butyl ester in a similar manner to (2b) butyl ester, vide supra, from (1c), squaric acid and (1f).

$\lambda_{max}$(MeOH) 638 nm $\delta_H$ (270 MHz;$CD_3OD$) 0.91 (3H,t, J=7.3 Hz), 1.02 (3H, t, J=7.3 Hz), 1.26–1.44 (2H, m), 1.44–1.64 (6H, m), 1.64–1.92 (6H, m), 1.77(12H, s), 2.34 (2H, t, J=7.1 Hz), 4.06 (2H, t, J=6.6 Hz), 4.15 (4H, app brt, J=6.9 Hz), 6.02 and 6.03 (each 1H, s), 7.28 (2H, app d, J=4.1 Hz), 7.86 (2H, app d, J=4.1 Hz) and 7.88 (2H, app s).

Subsequent hydrolysis gave the title compound as the potassium salt which was used in later studies.

2-(1-(5-Carboxypentyl)-3,3-dimethyl-5-sulphonato-2-indolinylidenemethyl)-4-(1-ethyl-3,3-dimethyl2-indolinylidenemethyl)cyclobutenediylium-1,3-diolate (2d)

The title compound was prepared as its butyl ester in a similar manner to (2b) butyl ester, vide supra, from (1c), squaric acid and (1g).

$\lambda_{max}$(MeOH) 630 nm $\delta_H$ (270 MHz;$CD_3OD$) 0.92 (3H, t), 1.27–1.92 (13H, m), 1.76 (12H, s), 2.34 (2H, t), 4.04 (2H, t), 4.11 (2H, br t), 4.23 (2H, br q), 5.95 and 6.05 (each 1H, s), 7.19–7.32 (3H, m), 7.33–7.45 (1H, m), 7.49 (1H, d) and 7.80 to 7.88 (2H, m).

Saponification of the above butyl ester (ca. 11 mg) and subsequent purification by chromatography (C18, $H_2O$/MeOH), in a similar manner to (2b), vide supra, afforded the title compound as the potassium carboxylate (8 mg)

$\delta_H$ (270 MHz;$CD_3OD$) 1.42 (3H, t), 1.46–1.58 (2H, m), 1.62–1.91 (4H, m), 1.76 and 1.78(each 6H, s), 2.19 (2H, t), 4.11 (2H, brt), 4.21 (2H, brt), 5.96 and 6.04 (each 1H, s), 7.20–7.34 (3H, m), 7.34–7.45 (1H, m), 7.45–7.51 (1H, m) and (7.83–7.89 (2H, m).

2-(1-(4-Sulphonatobutyl)-3,3-dimethyl-5-sulphonato-2-indolinylidenemethyl)-4-(1-(4-sulphonatobutyl)-3,3-dimethyl-5-carboxymethyl-2-indolinylidenemethyl)cyclobutenediylium-1,3-diolate Squaric acid (55 mg, 0.484 mmol) was dissolved in a mixture of acetic acid (5 ml), pyridine (5 ml) and acetic anhydride (500 μl) to give a clear yellow-orange solution. (1b) (200 mg, 0.484 mmol) was added in two portions (over 15 min) to give a green solution. After a further 15 min 1-(4-sulphonatobutyl)-2,3,3-trimethylindoleninium-5-acetic acid (1h) (85 mg) was added followed by a further portion (85 mg) after 35 min. The resultant dark green solution was stirred at ambient temperature for ca. 20 h, concentrated in vacuo and redissolved in $H_2O$/MeOH. Purification of the crude dye by HPLC (C18, $H_2O$/MeOH), with isolation of the middle one of three major blue components, afforded the title compound as the pyridinium salts. Percolation through an acid exchange resin (Dowex 50W, ca. 10 ml), eluting with water (25 ml), and concentration in vacuo of the eluent afforded the title compound as the free acids.

$\lambda_{max}$(MeOH) 638 nm $\delta_H$ (270 MHz;$D_2O$) 1.35 and 1.45 (each 6H, s), 1.75 (8H, br s), 2.80 (4H, app br t), 3.40 (2H, br s), 3.95 (4H, br m), 7.00–7.30 (4H, m) and 7.70 (2H, br s)

2-(1-Ethyl-3,3-dimethyl-5-sulphonato-2-indolinylidenemethyl)-4-(1-(5-carboxypentyl)-3,3-dimethyl-2-indolinylidenemethyl)cyclobutenediylium-1,3-diolate (2f)

The title compound was prepared as its butyl ester in a similar manner to (2b) butyl ester, vide supra, from (1e), squaric acid and (1i).

$\delta_H$ (270 MHz;$CD_3OD$) 0.92 (3H, t, $CH_2CH_2CH_3$), 1.00–1.90 (13H, m), 1.82 (12H, s, 2×$CMe_2$), 2.33 (2H, t, $CH_2CO_2H$), 4.02 (2H, t, $CO_2CH_2$), 4.08–4.25 (4H, m, 2×$CH_2N$), 5.96 and 6.03 (each 1H, s, vinylH), 7.16–7.55 (5H, series m, ArH) and 7.82–7.94 (2H, m, ArH).

Subsequent hydrolysis afforded the free acid.

$\delta_H$ (270 MHz;$CD_3OD$) 1.38 (3H, t, $CH_2CH_3$), 1.55 (2H, m), 1.62–1.95 (4H, m), 1.76 (12H, s, 2×$CMe_2$), 2.20 (2H, t, $CH_2CO_2H$), 4.10–4.25 (4H, m, 2×$NCH_2$), 5.95 and 6.05 (each 1H, s, vinylH), 7.18–7.50 (5H, series m, ArH) and 7.80–7.89 (2H, m, ArH).

2-(1-Benzyl-3,3-dimethyl-5-sulphonato-2-indolinylidenemethyl)-4-(1-(5-carboxypentyl)-5-sulphonato-3,3-dimethyl-2-indolinylidenemethyl)cyclobutenediylium-1,3-diolate (2g)

The title compound was prepared as its butyl ester in a similar manner to (2b) butyl ester, vide supra, from (1y), squaric acid and (1c).

$\delta_H$ (270 MHz; $D_2O$) 0.39 (3H, t, $CH_2CH_2CH_3$), 0.70–1.50 (22H, m), 1.88 (2H. br t, $CH_2CO_2H$), 3.58 (2H, br t, $CO_2CH_2$), 3.84 (2H, br, $NCH_2CH_2$), 4.96 (2H, br, $PhCH_2$), 5.63 and 5.67 (each 1H, overlapping br s, vinylH), 6.70–7.20 and 7.56–7.78 (11H, m, ArH).

Subsequent hydrolysis afforded the free acid.

$\delta_H$ (270 MHz; $CD_3OD$) 1.52 (2H, m), 1.63–1.90 (4H, m), 1.75 and 1.82 (each 6H, s, 2×$CMe_2$), 4.16 (2H, br t, $NCH_2CH_2$), 5.37 (2H, br s, $PhCH_2$), 6.03 and 6.07 (each 1H, s, vinylH), 7.16–7.40 (7H, m, ArH) and 7.72–7.93 (4H, m, ArH).

2-(1-(5-Carboxypentyl)-3,3-dimethyl-5-sulphonato-2-benzindolinylidenemethyl)-4-(1-ethyl-3,3-dimethyl-5-sulphonato-2-benzindolinylidenemethyl)-cyclobutenediylium-1,3-diolate (2h)

The title compound was prepared in a similar manner to (2e) from (1u), (1v) and squaric acid in a two step procedure with isolation of the intermediate 'half dye'.

$\lambda_{max}$(MeOH)=664 nm

MALDI-TOF ($C_{42}H_{43}N_2S_2O_8$ requires $M^+$802) 824 ($M^+$+Na), 711

2-(1-(5-Carboxypentyl)-3,3-dimethyl-5-sulphonato-2-benzindolinylidenemethyl)-4-(1-ethyl-3,3-dimethyl-2-benzindolinylidenemethyl)-cyclobutenediylium-1,3-diolate (2i)

The title compound was prepared in a similar manner to (2b) from (1k), (1v) and squaric acid.

λ$_{max}$(MeOH)=662 nm

δ$_H$ (270 MHz; CD$_3$OD) 1.15 (3H, t, CH$_2$CH$_3$), 1.25 (2H, m), 1.44 (2H, m), 1.88 (2H, m), 1.99 (12H, s, 2×CMe$_2$), 2.25 (2H, brt, CH$_2$CO$_2$H), 4.19 (2H, br t), NCH$_2$CH$_2$), 4.27 (2H, br q, CH$_2$CH$_3$), 5.99 and 6.04 (each 1H, s, vinylH), 7.41 (1H, app t, ArH), 7.56 (3H, m, ArH), 7.92 (2H, app t, ArH), 8.01 (2H, app t, ArH), 8.24 (2H, m, ArH) and 8.41 (1H, s, ArH).

For examples of dyes bearing free hydroxyl groups see Examples 11 and 12.

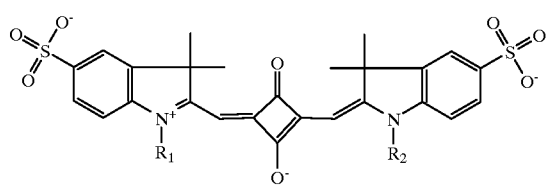

(2a) R$_1$ = (CH$_2$)$_4$SO$_3^-$
R$_2$ = (CH$_2$)$_5$CO$_2$H
(2b) R$_1$ = (CH$_2$)$_5$CO$_2$H
R$_2$ = Et
(2c) R$_1$ = (CH$_2$)$_5$CO$_2$H
R$_2$ = Bu
(2g) R$_1$ = Bn
R$_2$ = (CH$_2$)$_5$CO$_2$H

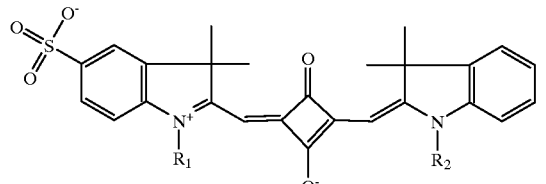

(2d) R$_1$ = (CH$_2$)$_5$CO$_2$H
R$_2$ = Et
(2f) R$_1$ = Et
R$_2$ = (CH$_2$)$_5$CO$_2$H

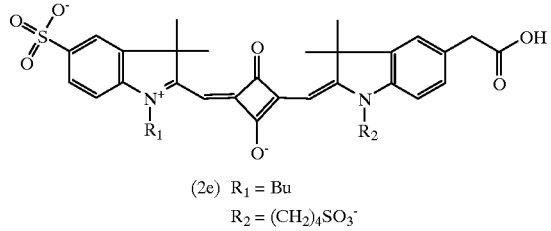

(2e) R$_1$ = Bu
R$_2$ = (CH$_2$)$_4$SO$_3^-$

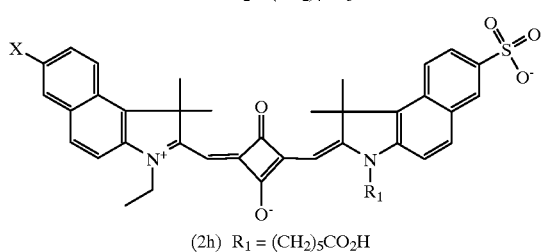

(2h) R$_1$ = (CH$_2$)$_5$CO$_2$H
X = SO$_3^-$
R$_1$ = (CH$_2$)$_5$CO$_2$H
X = H

EXAMPLE 3

Synthesis of sulphonic acid substituted squarate dyes from indoleninium and thiazolinium intermediates 2-(1-(5-Carboxypentyl)-3,3-dimethyl-5-sulphonato-2-indolinylidenemethyl)-4-(3-ethyl-2-benzothiazolinylidenemethyl)cyclobutenediylium-1,3-diolate (3a)

Synthesised in an analogous manner to Example (2b) from intermediates (1c), (1s), squaric acid and additional quinoline as base to give a crude mixture of dye products. Hydrolysis of the crude material, purification by HPLC and percolation through H$^+$ exchange resin afforded the title compound.

λ$_{max}$(MeOH) 636 nm

δ$_H$ (270 MHz; DMSO-d6) 1.18–1.82 (9H, m), 1.64 (6H,s, 2×Me), 3.96 (2H, br), 4.45 (2H, br), 5.57 and 6.09 (each 1H, br s, vinyl-CH), 7.11 (1H, m, ArH), 7.40 (1H, m, ArH), 7.48–7.70 (3H, m, ArH), 7.77 (1H, m, ArH) and 8.07 (1H, d, ArH)

2-(3-Ethyl-2-benzothiazolinylidenemethyl)-4-(1-(4-sulphonatobutyl)-3,3-dimethyl-5-carboxymethyl-2-indolinylidenemethyl)cyclobutenediylium-1,3-diolate (3b)

Synthesis in an analogous method to Example (3a) from intermediates (1h) and (1s), with purification by HPLC only, afforded the mono-quinolinium salt of the title compound.

λ$_{max}$(MeOH) 642 nm δ$_H$ (270 MHz; CD$_3$OD) 1.43 (3H, t, CH$_2$CH$_3$), 1.68 (6H, s, 2×Me), 1.96 (4H, br), 2.91 (2H, br, CH$_2$SO$_3^-$), 3.63 (2H, s, ArCH$_2$), 4.05 (2H, br, NCH$_2$CH$_2$), 4.40 (2H, brq, NCH$_2$CH$_3$), 5.75 and 6.07 (each 1H, br s, vinyl—CH), 7.13 (1H, d, ArH), 7.23 (1H, d, ArH), 7.32 (1H, s, ArH), 7.38 (1H, t, ArH), 7.46–7.66 (2H, m, ArH), 7.75–7.95 (3H, m, ArH), 8.04 (1H, t, ArH), 8.18 (2H, t, ArH), 8.86 (1H, d, ArH) and 9.05 (1H, d, ArH)

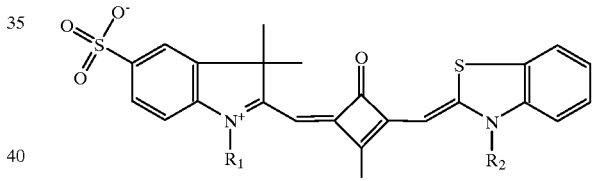

(3a) R$_1$ = (CH$_2$)$_5$CO$_2$H
R$_2$ = Et

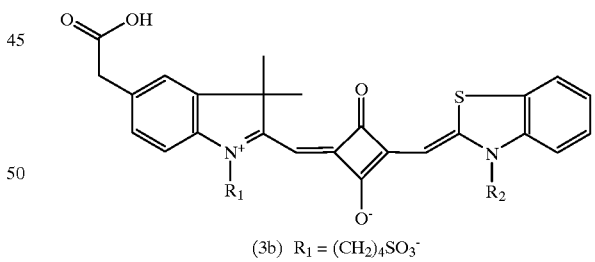

(3b) R$_1$ = (CH$_2$)$_4$SO$_3^-$
R$_2$ = Et

EXAMPLE 4

Synthesis of the succinimidyl esters of the carboxylic acid derivatives of squarate dyes A representative procedure for activation is as below, which is given for example (2b)

To a solution of carboxylic acid derivative (2b) (potassium salt) (8 mg, 0.01 mmol) in DMF (1 ml) was added diisopropylethylamine (10.5 μl, 0.06 mmol) and O-(N-succinimidyl)-N,N,N',N'-tetramethyluronium tetrafluoroborate (TSTU) (9 mg, 0.03 mmol). The reaction was monitored by HPLC (C18, 25 mM pH7 Phosphate buffer/

MeCN) and upon completion was sealed under nitrogen and stored in a freezer until required for labelling experiments.

The follow squaric acid dyes were activated in an analogous manner:

(2a, c–h), (3a) and (3b).

EXAMPLE 5

Use of squaric acid derived fluorophores for automated fluorescent DNA sequencing Primer synthesis An M13 (–20) universal 18 mer primer was prepared according to established methods on an ABI model 394 DNA synthesiser. The 5' terminus of the oligonucleotide was modified by coupling an aliphatic amine group in the final synthesis cycle by means of a trifluoroacetamide protected-aminolinker amidite [Pharmacia Biotech]. The primer sequence used was $NH_2$-tgtaaaacgaacggccagt. The crude primer was deprotected in 30% $NH_4OH$ for 16 hours at 55° C. then purified free of organic by-products and amines using phenol/chloroform extraction followed by ethanol precipitation. DNA was dissolved in water at 1 OD unit/μl and stored at –70° C.

Primer labelling.

N-hydroxy succinimidyl esters of the squarate dyes were supplied in DMF or MeCN at 4–10 mg/ml. To label the primers, 40 μl of dye solution was mixed with 50 μl of 100 mM sodium phosphate buffer at pH 8.0 and 10 μl [10 OD or 300 μg] of $NH_2$-oligonucleotide. For squaric acid dyes not bearing any sulphonic acid groups (therefore with an overall neutral charge) and which are less soluble in 40% DMF, 1–4 dioxan was added to 10–20% v/v final concentration in order to keep the dye in solution and raise the labelling efficiency. Reactions were allowed to continue at +4° C. in the dark for between 6–16 h. Reactions were stopped by addition of sodium acetate pH 5.0 to a final concentration of 300 mM followed by 3 aqueous volumes of 99.8% ethanol to precipitate the oligonucleotide and remove unincorporated dye. After centrifugation at 13000 g for 15 minutes the DNA pellet was washed in 80% ethanol, dried in vacuo and dissolved in 100 μl of TE buffer at pH 8.0.

Primer purification

Squaric acid dye labelled primers were separated from residual, non-covalently attached dye and from unlabelled primer by HPLC on a 24 cm×0.5 cm Spherisorb ODS2 column with a 5 μm support size. A 1 ml/minute gradient from 95% solvent A/5% solvent B to 30% solvent A/70% solvent B was used. A=0.1M sodium acetate pH6.8, B=acetonitrile. Fractions absorbing at both 260 nm and 635 nm were collected and dried in a vacuum centrifuge. Fractions were pooled in 100 μl of TE buffer and ethanol precipitated as above to desalt them prior to sequencing.

DNA sequencing 2 pmol of squarate dye-primer was mixed with 0.2 pmol of M13 mp8 phage DNA in a volume of 25 μl. The primer/template mixture was divided into four 6 μl aliquots designated A, C, G & T. 2 μl of the appropriate enzyme nucleotide/buffer/premix from Amersham kit RPN2437 [Thermo Sequenase™ labelled primer sequencing kit] was added and the reactions were placed in Perkin-Elmer Gene-Amp PCR system 9600 thermocycler. Samples were taken through 25 cycles at 95° C./30 seconds: 60° C./30 seconds. After thermocycling, 3 μl of loading dye containing 90% formamide/5 mM EDTA was added, the reactions were concentrated in vacuum centrifuge for 10 minutes and then heat denatured at 80° C. for 2 minutes before loading on 6.1 M urea/5% HydroLink gel in a Vistra DNA sequencer 725.

Electrophoresis and detection

A Vistra DNA sequencer 725 was modified by replacement of the laser with a 30 mW Helium-Neon 632 nm tube and HV power supply. The optical filter was changed to a 645 nm long-pass. No other alterations were necessary to detect SQ5 fluorescence. Gels were run for 8–10 hours at 1400 V and maintained at or above 35° C. throughout. Image data was analysed using Vistra V2.01 software and Molecular Dynamics' ImageQuaNT program.

Results

All of the Examples (2a–h) and (3a–b) gave sequence data. The signal strength and peak resolution values were comparable to a commercially available cyanine dye (Cy5™) commonly used for sequencing. Base-calling accuracies of more than 98% to 550 bases are typical.

EXAMPLE 6

The use of dye labelled oligonucleotides in two colour detection

An 18 mer oligonucleotide was labelled separately with two cyanine dyes (6a) and (6b) and an invention dye (2f). The excitation and emission maxima of these dye oligonucleotide conjugates are shown in Table 1. 100 fmoles of each labelled oligonucleotide was loaded in the following pairs into the same well onto a 19% denaturing acrylamide gel:

1. (6a) and (6b)
2. (6a) with (2f)
3. (2f) with (6b)

The labelled oligonucleotides were also loaded individually.

After electrophoresis under denaturing conditions the gel was scanned in a prototype scanning fluorescence instrument with a 633 nm helium neon laser excitation light source. Fluorescent emission was collected in 3 sequential scans. The first scan with a 645 nm RG filter (Schott) in place collected all the fluorescent light produced. The second and third scans were with 660 nm $df_{30}$ and 700 nm eflp filters (Omega Optical) to collect and discriminate the fluorescence from each dye.

Each pair of dyes was identified from the 645 nm RG filter image of the gel and sampled in a fluorochrome separation algorithm to identify the spectral properties of each dye. The images from each scan were processed to produce overlaid 2 colour images.

These images show that (6a) with (6b) and (2f) with (6b) can be used as dye 2 colour pairs. These dyes are efficiently excited at the 633 nm excitation wavelength and can be spectrally separated and identified for 2 colour applications.

Notes

The 645 nm RG is a red glass long pass filter which excludes light below 645 nm.

The 660 $df_{30}$ filter is a band pass filter centred at 660 nm with +/–15 nm tolerance i.e. collects a band of light from 645–675 nm. The 700 eflp filter is a long pass filter which should exclude light below 700 nm i.e. collects from 700 nm upwards.

TABLE 1

Spectral Properties of Dye-Oligonucleotide Conjugates

| DYE 18 MER | $EX_{MAX}$ IN $TE_8$ BUFFER | $EM_{MAX}$ IN $TE_8$ BUFFER |
| --- | --- | --- |
| 2f | 630 nm | 642 nm |
| 6a | 650 nm | 660 nm |
| 6b | 680–685 nm | 700 nm |

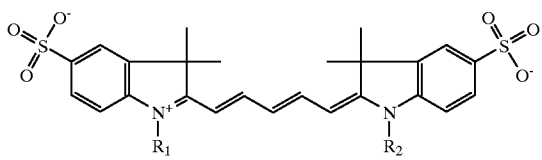

(6a) R$_1$ = (CH$_2$)$_4$SO$_3^-$
R$_2$ = (CH$_2$)$_3$OCH$_2$CO$_2$H

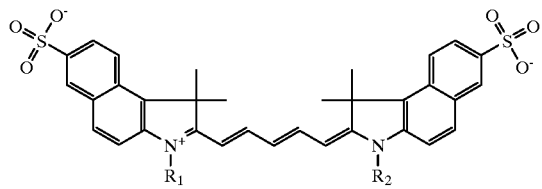

(6b) R$_1$ = (CH$_2$)$_4$SO$_3^-$
R$_2$ = (CH$_2$)$_3$OCH$_2$CO$_2$H

EXAMPLE 7

Modifications of the central cyclobutenediylium-1,3-diolate ring of squarate dyes 2,4-Bis(1-ethyl-3,3-dimethyl-2-indolinylidenemethyl) cyclobutenediylium-1,3-diolate (7a)

1-Ethyl-2,3,3-trimethylindoleninium iodide (1g) (3.15 g, 10 mmol), squaric acid (0.57 g, 5 mmol) and n-butanol (40 ml) were mixed and heated at reflux for 16 h. The solvent was then evaporated and the product dye (7a) isolated by flash chromatography (0–5% MeOH/CH$_2$Cl$_2$). Yield=1.7 g (75%)

$\lambda_{max}$ (MeOH)=628 nm, $\lambda_{ex}$=626 nm, $\lambda_{em}$(MeOH)=635 nm $\delta_H$ (270 MHz, CDCl$_3$) 7.4–6.9 (8H, m), 6.0 (2H, s), 4.1 (4H, q), 1.8 (12H, s), 1.4 (6H, t).

Also isolated was the half-dye species 3-butoxy-4-(1-ethyl-3,3-dimethyl-2-indolinylidenemethyl)-cyclobut-3-en-1,2-dione (7b).

$\lambda_{max}$ (MeOH)=424 nm.

$\delta_H$ (270 MHz, CDCl$_3$) 7.4–6.8 (4H, m), 5.4 (1H, s), 4.85 (2H, t), 3.9 (2H, q), 1.9 (2H, m), 1.7 (6H, s), 1.5 (2H, m), 1.35 (3H, t), 1.0 (3H, t).

3-Methoxy-2,4-bis(1-ethyl-3,3-dimethyl-2-indolinylidenemethyl)cyclobutenediylium-1-olate methosulphate (7c)

The squarylium dye (7a) (1.0 g, 2.2 mmol) was dissolved in chloroform (20 ml) to give a deep blue solution. To this was added dimethyl sulphate (5 ml); the mixture was then heated at reflux for 16 h. The resulting solution was cooled, washed well with water, then dried (Na$_2$SO$_4$), filtered and evaporated to low volume. Diethyl ether was then added slowly, with scratching, up to about 100 ml. This caused the methylated product (7c) to crystallize out as metallic green needles, which were collected by filtration, washed with fresh ether and dried under vacuum. Yield=1.24 g (95%).

$\lambda_{max}$ (MeOH)=630 nm, $\lambda_{ex}$(625), $\lambda_{em}$(MeOH)=638 nm $\delta_H$ (270 MHz, CDCl$_3$) 7.43–7.38 (4H, m), 7.30 (2H, d), 7.18 (2H, d), 4.86 (3H, s), 4.3 (4H, q), 3.74 (3H, s), 1.73 (12H, s), 1.46 (6H, t).

(7c) is reactive, the O—Me group being readily replaced by an alcohol or an amine. This is illustrated below.

3-Butoxy-2,4-bis(1-ethyl-3,3-dimethyl-2-indolinylidenemethyl)cyclobutenediylium-1-olate (7d)

The dye (7c) (50 mg, 0.086 mmol) was dissolved in n-butanol (3 ml) and heated at 70° C., with monitoring by t.l.c. (silica, 15% MeOH/CH$_2$Cl$_2$). Once all the starting dye had been consumed (3–4 h) the solution was cooled and evaporated. The residue was dissolved in chloroform (1 ml) and diluted with diethyl ether (15 ml); after standing in the freezer for 16 h the product (7d) separated as metallic green needles. Yield=36 mg (anion undetermined).

$\lambda_{max}$ (MeOH)=628 nm.

$\delta_H$ (270 MHz, CDCl$_3$) 7.5–7.0 (8H, m), 5.9 (2H, s), 5.2 (2H, t), 4.3 (4H, q), 4.1 (2H, t), 2.1 (2H, m), 1.8 (12H, s), 1.75–1.4 (m), 1.1 (3H, t), 0.9 (3H, t).

3-Butylamino-2,4-bis(1-ethyl-3,3-dimethyl-2-indolinylidenemethyl)cyclobutenediylium-1-olate (7e)

The dye (7c) (200 mg, 0.35 mmol) was dissolved in dichloromethane (20 ml). To the stirred solution was added a solution of n-butylamine in dichloromethane (approx. 1 drop per ml CH$_2$Cl$_2$), in 0.1 ml portions. After each addition, the mixture was analyzed by t.l.c. (silica, 15% MeOH/CH$_2$Cl$_2$), until no more starting dye was present. The mixture was then evaporated and the residue purified by flash chromatography (silica, 4–10% MeOH/CH$_2$Cl$_2$). This gave 154 mg of the title dye (7e) as an amorphous powder after evaporation (anion undetermined).

$\lambda_{max}$ (MeOH)=646 nm.

$\delta_H$ (270 MHz, CDCl$_3$) 9.5 (1H, broad t), 7.6–6.9 (8H, m), 6.5 (1H, s), 5.7 (1H, s), 4.7 (2H, q), 4.0 (2H, q), 3.8 (2H, broad q), 1.9 (2H, m), 1.8 (12H, 2×s), 1.6 (2H, m), 1.5 (3H, t), 1.4 (3H, t), 1.0 (3H, t).

3-(7-(4,4'-Dimethoxytrityloxy)-6-hydroxy-4-oxaheptyl)amino-2,4-bis(1-ethyl-3,3-dimethyl-2-indolinylidenemethyl)-cyclobutenediylium-1-olate (7f)

The dye (7c) (58 mg, 0.1 mmol) was dissolved in dichloromethane (4 ml); to this was added a solution of 7-(4,4'-dimethoxytrityloxy)-6-hydroxy-4-oxaheptylamine (EP 0527184B1) (ca.0.3 mmol in 2 ml in dichloromethane) in portions, until t.l.c. analysis (silica, 15% MeOH/CH$_2$Cl$_2$) indicated complete reaction. The solution was then evaporated and the residue purified by flash chromatography (silica, 4–10% MeOH/CH$_2$Cl$_2$). Evaporation gave 85 mg of the product (7f) as a violet-blue foam (anion undetermined).

$\lambda_{max}$ (CH$_2$Cl$_2$)=652 nm; $\lambda_{max}$ (CH$_2$Cl$_2$+CCl$_3$CO$_2$H)= 652++504 nm.

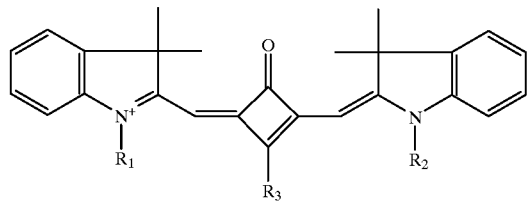

(7a) R$_1$ = R$_2$ = Et  R$_3$ = O$^-$
(7c) R$_1$ = R$_2$ = Et  R$_3$ = OMe  MeOSO$_3^-$
(7d) R$_1$ = R$_2$ = Et  R$_3$ = OBu
(7e) R$_1$ = R$_2$ = Et  R$_3$ = NHBu

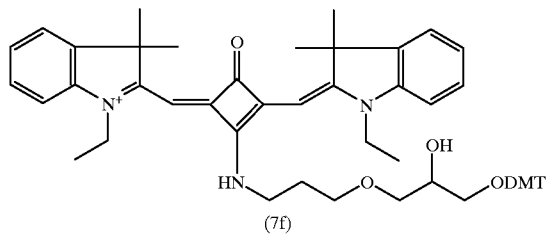

(7f)

The above were used in DNA sequencing experiments using methods similar to those outlined in Example 5. The results were excellent. However, the method of labelling was not via the succinimidyl ester but by direct displacement of the dye ether linkage by the 5' amino substituent on the primer.

EXAMPLE 8

An active ester derivative of a cyclobutenediylium-1,3-diolate ring modified squarate dye 3-(N-Methyl-N-(3-carboxypropyl))amino-2,4-bis(1-ethyl-3,3-dimethyl-2-indolinylidenemethyl)-cyclobutenediylium-1-olate chloride (8a)

4-Methylaminobutanoic acid.HCl (154 mg, 1.0 mmol) was mixed with methanol (10 ml). To this was added a solution of tetrabutylammonium hydroxide in methanol (1.0 M, 2.0 ml, 2.0 mmol). The methylated dye (7c) was then added (289 mg, 0.5 mmol) and the mixture stirred for a further 15 min. This solution was poured into chloroform and washed three times with a large volume of water, then with saturated aqueous sodium bicarbonate solution, and finally with 0.1M HCl. The organic solution was dried ($Na_2SO_4$), filtered and evaporated; the residue was then purified by flash chromatography (silica, 5–20% MeOH/$CH_2Cl_2$), to give 212 mg (72%) of the title dye (8a) as a violet-blue powder.

$\lambda_{max}$ (MeOH) 660 nm, $\lambda_{ex}$=657 nm, $\lambda_{em}$(MeOH)=670 nm
$\delta_H$ (270 MHz, $CDCl_3$) 7.5–7.0 (8H, m), 6.0 (2H, s), 4.3 (4H, q), 3.85 (3H, s), 2.6 (2H, m), 2.2 (2H, m), 1.7 (12H, s), 1.4 (6H, s).

TABLE 8.1

Example of decrease in fluorescence for dye (8a)

| EXAMPLE NO. | VISIBLE ABSORBANCE (AU) | RELATIVE FLUORESCENCE INTENSITY |
|---|---|---|
| (7a) | 0.489 | 713 |
| (8a) | 0.486 | 21 |

Synthesis of the succinimidyl ester of the dye (8a)

The dye (8a) (59 mg, 0.1 mmol) was dissolved in dichloromethane (2 ml). To this solution was added a solution of N-hydroxysuccinimide (12 mg, 0.1 mmol) in acetonitrile (2 ml), followed by a solution of N,N'-dicyclohexylcarbodiimide in dichloromethane (1.0M, 0.12 ml, 0.12 mmol). This mixture was stirred for 24 h, then it was filtered and evaporated. The residue was purified by flash chromatography (silica, 5–20% MeOH/$CH_2Cl_2$) to give the active ester as a solid with a metallic red lustre. Yield=55 mg (80%).

$\lambda_{max}$ (MeOH)=660 nm
$\delta_H$ (270 MHz, $CDCl_3$) 7.6–7.0 (8H, m), 6.0 (2H, s), 4.3 (4H, >>q), 4.0 (2H, broad s), 3.7 (3H, s), 2.9 (2H, m), 2.7 (4H, s), 2.3 (2H, m), 1.7 (12H, s), 1.4 (6H, app t).

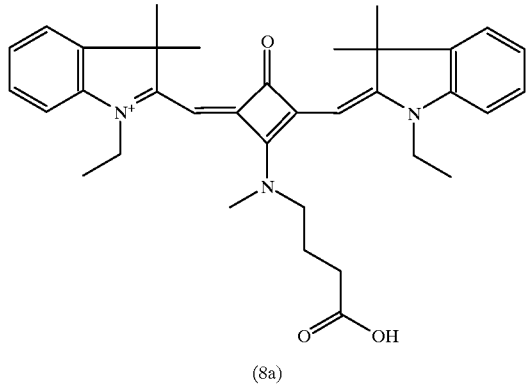

(8a)

EXAMPLE 9

Modifications to the central cyclobutenediylium-1,3-diolate ring of a thiazolinium based squarate dye 2,4-Bis-(3-ethyl-2-benzothiazolinylidenemethyl)-cyclobutenediylium-1,3-diolate (9a)

3-Ethyl-2-methylbenzothiazolium iodide (1s) (1.55 g, 5.0 mmol), squaric acid (0.285 g, 2.5 mmol), quinoline (1.5 ml) and n-butanol (20 ml) were mixed and heated at reflux for 7 h under nitrogen atmosphere. The resulting dark green mixture was cooled in the fridge overnight, then the solid collected by filtration. This solid was washed with a little ice-cold methanol, then diethyl ether, and dried under vacuum to give the title dye (9a) as a dark powder with a metallic olive-green lustre. Yield=0.73 g (68%).

$\lambda_{max}$ (MeOH)=650 nm. $\lambda_{em}$ (MeOH) 660 nm.
$\delta_H$ (270 MHz, $CDCl_3$) 7.6–7.0 (8H, m), 5.9 (2H, s), 4.2 (4H, q), 1.4 (6H,t).

3-Methoxy-2,4-bis(3ethyl-2-benzothiazolinylidenemethyl)-cyclobutenediylium-1-olate methosulphate (9b)

Dye (9a) (0.73 g, 0.7 mmol) was dissolved in chloroform (30 ml); to the resultant deep blue solution was added dimethyl sulphate (3 ml). This mixture was heated at reflux for 7 h, then left to stand for three days. It was then washed with water; the organic layer was retained and the aqueous layer extracted with more chloroform. The combined organic extracts were dried ($MgSO_4$), filtered and the solvent removed under reduced pressure, to a volume of ca. 15 ml. Diethyl ether (40 ml) was added to precipitate the product, which was collected by filtration, washed with ether and dried under vacuum to give the titled dye (9b) (1.0 g, 100%). T.l.c. (silica; 15% methanol/dichloromethane. (9a), $R_f$=0.75→(9b), $R_f$=0.3).

$\lambda_{max}$ (MeOH) 632 nm; $\lambda_{ex}$ (MeOH) 649 nm, $\lambda_{em}$ (MeOH) 658 nm.

$\delta_H$ (300 MHz, $CDCl_3$) 1.29 (6H, t, J 7.0 Hz, 2×benzothiazole N—$CH_2$—$CH_3$), 3.36 (3H, s, methosulphate —$CH_3$), 4.44 (4H, q, J 7.0 Hz, 2×benzothiazole N—C$H_2$—$CH_3$), 4.51 (3H, s, squarate —OMe), 6.00 (2H, s, 2×methine=C$H$—), 7.37 (2H, app t), 7.53 (2H, app t), 7.72 (2H, d, J 8.4 Hz), 8.01 (2H, d, J 8.1 Hz).

3-Butylamino-2,4-bis(3-ethyl-2-benzothiazolinylidenemethyl)-cyclobutenediylium-1-olate methosulphate (9c)

Methylated dye (9b) (100 mg) was mixed with dichloromethane (30 ml) and n-butylamine (0.2 ml). This mixture was stirred at room temperature for 30 mins, during which time all the solid dissolved. T.l.c. (silica; 15% methanol/dichloromethane. (9b), $R_f$=0.3→(9c), $R_f$=0.45). The solvent was removed under reduced pressure and the blue product isolated by flash chromatography (silica; 4–10% methanol//chloroform); the crude product gum was triturated with diethyl ether to give a solid with a metallic red lustre, 43 mg.

$\lambda_{max}$ (MeOH) 658 nm; $\lambda_{ex}$ (MeOH) 657 nm, $\lambda_{em}$ (MeOH) 671 nm.

$\delta_H$ (300 MHz, $CDCl_3$) 0.96 (3H, t, J 7.3 Hz, butyl —$CH_3$), 1.36–1.51 (8H, m, 2×benzothiazole N—$CH_2$—C$H_3$+—$CH_2$—), 1.83 (2H, m, —$CH_2$—), 3.56 (2H, q, J 7.1 Hz, —HN—$CH_2$—), 4.11+4.47 (each 2H, q, J 7.0 Hz, 2×benzothiazole N—$CH_2$—$CH_3$), 5.631 (1H, s, methine=C$H$—), 7.08–7.59 (9H, m, 8×benzothiazole aryl-H+ methine=C$H$—), 10.17 (1H, broad app. t).

3-(N-methyl-N-(3-carboxypropyl))amino-2,4-bis(3-ethyl-2-benzothiazolinylidenemethyl)-cyclobutenediylium-1-olate chloride (9d)

4-(Methylamino)butanoic acid.HCl (0.31 g, 2.0 mmol) was dissolved in methanol (10 ml). To this solution was added a solution of tetra-n-butylammonium hydroxide in methanol (1M, 4 ml, 4.0 mmol), followed by dye (9b) (0.58 g, 1.0 mmol). The deep blue solution that resulted was stirred for 40 mins; t.l.c. (silica; 15% methanol/dichloromethane. (9b), $R_f$=0.3→(9d), $R_f$<0.1).

The solvent was removed under reduced pressure and the residue triturated with water. The metallic bronze solid was collected by filtration, washed with water and acetone, then dried under vacuum to give the acid dye (9d), 0.435 g (82%).

$\lambda_{max}$ (MeOH) 670 nm; $\lambda_{ex}$ (MeOH) 670 nm, $\lambda_{em}$ (MeOH) 686 nm.

$\delta_H$ (300 MHz, CD$_3$OD) 1.31 (6H, t, 2×benzothiazole N—CH$_2$—C$\underline{H}_3$), 1.90 (2H, m, —CH$_2$—C$\underline{H}_2$—CH$_2$), 2.23 (2H, app t, —C$\underline{H}_2$—CO$_2$H), 3.30 (3H, s, N—C$\underline{H}_3$), 3.45 (2H, app t, MeN—C$\underline{H}_2$—), 4.28 (4H, broad s, 2×benzothiazole N—C$\underline{H}_2$—CH$_3$), 5.80 (2H, s, 2×methine=C$\underline{H}$—), 7.23 (2H, d), 7.36 (4H, broad m), 7.67 (2H, m).

TABLE 9.1

Example of the decrease in fluorescence for dye (9d)

| EXAMPLE NO. | VISIBLE ABSORBANCE (AU) | RELATIVE FLUORESCENCE INTENSITY |
|---|---|---|
| (9a) | 0.490 | 1140 |
| (9d) | 0.485 | 124 |

3-(3-(tert-Butoxycarbonylamino)propylamino)-2,4-bis(3-ethyl-2-benzothiazolinylidenemethyl)-cyclobutenediylium-1-olate methosulphate (9e)

Synthesised in an analogous manner to (9c) using tert-butyl-N-(3-aminopropyl)carbamate.

$\lambda_{max}$ (MeOH)=656 nm $\delta_H$ (300 MHz, CDCl$_3$) 1.40 (9H, s, CMe$_3$), 1.48 (6H, t, J 6.6, 2×CH$_2$CH$_3$), 1.97 (2H, m, NHCH$_2$CH$_2$), 3.30 (2H, br q, CH$_2$NH), 3.67 (2H, br q, CH$_2$NH), 3.74 (3H, s, MeOSO$_3^-$), 4.13 and 4.44 (each 2H, br q, CH$_2$CH$_3$), 5.69 (1H, s, vinylH), 5.89 (1H, brt, NHBOC), 6.58 (1H, s, vinylH), 7.12–7.60 (8H, series m, ArH) and 8.83 (1H, br t, vinylNH).

DNA sequencing experiments

Dye primer synthesis and subsequent sequencing experiments were carried out in a similar manner to that outlined in Example 5 with labelling by either the succinimidyl ester or the ether derivative of the above dyes. The results were excellent.

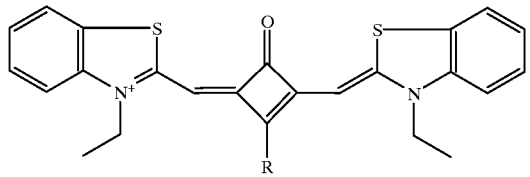

(9a) R = O$^-$
(9b) R = OMe MeOSO$_3^-$
(9c) R = NHBu
(9d) R = N(Me)CH$_2$CH$_2$CH$_2$CO$_2$H Cl$^-$
(9e) R = NH(CH$_2$)$_3$NHBOC

EXAMPLE 10

Synthesis of a centrally modified croconic acid based dye
Croconic acid dye (10a)

The dye (10a) was prepared according to the procedure outlined in U.S. Pat. No. 3,793,313 (1974).

$\lambda_{max}$ (MeOH) 754 nm

Methylation of (10a) to give (10b)

Dye (10a) (250 mg, 0.54 mmol) was dissolved in chloroform (12 ml) to give a dark olive-green solution. To this was added dimethyl sulphate (1.5 ml) and the mixture was heated at 60° C. for 4 h, giving a purple solution. T.l.c. (silica; 15% methanol/dichloromethane. (10a) yellow-green, dries to blue, $R_f$=0.6→(10b) purple, $R_f$=0.4). The solvent was removed under reduced pressure to a volume of ca. 2 ml, then it was diluted with diethyl ether. The precipitated solid was collected by filtration, washed with more ether and dried under vacuum to give (10b), 330 mg (100%).

$\lambda_{max}$ (MeOH) 764 nm

Coupling of (10b) to n-butylamine to give (10c)

Methylated dye (10b) (20 mg) was dissolved in dichloromethane (5 ml); to this was added n-butylamine (1 drop). The colour of the solution changed quickly from purple to an orange-brown. T.l.c. (silica; 15% methanol/dichloromethane. (10b) purple, $R_f$=0.4→(10c) orange-brown, dries to purple, $R_f$=0.55). The solution was purified by flash chromatography (silica; 10% methanol/dichloromethane) to give the amino dye (10c), 15 mg.

$\lambda_{max}$ (MeOH) 768 nm $\delta_H$ (270 MHz;CDCl$_3$) 0.98 (3H, t, CH$_3$CH$_2$CH$_2$), 1.50–2.00 (10H, m, 2×CH$_2$CH$_3$ and NCH$_2$CH$_2$CH$_2$), 4.30 (2H, m, NHCH$_2$), 4.50 and 4.90 (each 2H, br q, 2×CH$_2$CH$_3$), 6.50 (1H, s, vinylH), 7.2–7.8 (9H, m, vinylH+8×arylH) and 11.15 (1H, br, NHCH$_2$).

Coupling of (10b) to 4-(methylamino)butanoic acid 4-(Methylamino)butanoic acid .HCl (31 mg, 0.2 mmol) was dissolved in methanol (5 ml), then a solution of tetra-n-butylammonium hydroxide in methanol (1M, 0.4 ml, 0.4 mmol) added. To this was added (10b) (60 mg, 0.1 mmol), giving a brownish solution. T.l.c. (silica; 15% methanol/dichloromethane. (10b) purple, $R_f$=0.4→(10d) brown, $R_f$<0.1). The solvent was then removed under reduced pressure and the residue purified by preparative t.l.c. (silica; methanol 40%; chloroform 60%) to give the acid dye (10d), 20 mg.

$\lambda_{max}$ (MeOH) 788 nm

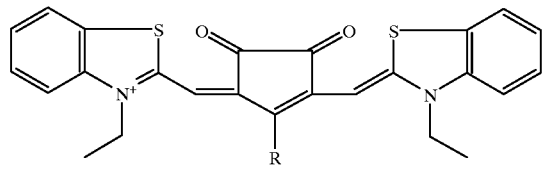

(10a) R = O$^-$
(10b) R = OMe MeOSO3$^-$
(10c) R = NHBu
(10d) R = N(Me)CH$_2$CH$_2$CH$_2$CO$_2$H

EXAMPLE 11

Synthesis of phosphoramidite derivatives of squarate dyes
Synthesis of dye phosphoramidite (11c)
3-Methoxy-4-(1-ethyl-3,3-dimethyl-5-sulphonato-2-indolinylidenemethyl)cyclobut-3-en-1,2-dione, sodium salt (11a)

1-Ethyl-2,3,3-trimethylindoleninium-5-sulphonate (1e) (1.33 g, 5 mmol) was dissolved in dry methanol (12 ml); to the resulting solution was added sodium methoxide (0.27 g, 5 mmol) and the mixture stirred until all the solid had dissolved (5 min). 3,4-Dimethoxycyclobut-3-en-1,2-dione (0.71 g, 5 mmol) was then added and the resulting mixture heated at reflux under nitrogen atmosphere for 4 h. The greenish-yellow mixture was then cooled at 0° C. for 16 h. The precipitated yellow solid was collected by filtration, washed with ice-cold ethanol and diethyl ether, then dried under vacuum at 50° C. to give the title compound (11a), 0.67 g (34%).

$\lambda_{max}$ (MeOH) 422 nm $\delta_H$ (270 MHz, CD$_3$OD) 1.3 (3H, t, indole N—CH$_2$—CH$_3$), 1.6 (6H, s, indole CMe$_2$), 4.0 (2H, g, indole N—CH$_2$—CH$_3$), 4.6 (3H, s, —OMe), 5.6 (1H , s, methine —CH=), 7.1 (1H, d), 7.8 (2H, m).

2-(1-Ethyl-3,3-dimethyl-5-sulphonato-2-indolinylidenemethyl)-4-(1-(5-hydroxypentyl)-3,3-dimethyl-2-indolinylidenemethyl)-cyclobutenediylium-1,3-diolate (11b)

Intermediate (1m) (415 mg, 1.0 mmol) and half-dye (11a) (350 mg, 0.89 mmol) were mixed in dry 1-butanol (10 ml) and the mixture heated at reflux for 6 h, giving a deep blue solution. The reaction was then deemed to be complete by UV/VIS (methanol solution, $\lambda_{max}$ 632 nm) and t.l.c. (C- 18 silica; ethanol 50%:water 50%. One blue spot at R$_f$=0.3).

The acetate-dye was not isolated; the solvent was removed under reduced pressure and the residue redissolved in methanol (5 ml). To this solution was added potassium carbonate (200 mg) and the mixture stirred for about 1 h (C-18 silica; ethanol 50%:water 50%. Dye-OAc, R$_f$=0.3→(11b), R$_f$=0.4). This mixture was purified by prep. HPLC (C-18 column; water→methanol gradient) to give the title compound (11b), 450 mg.

$\lambda_{max}$ (MeOH) 632 nm $\delta_H$ (300 MHz, DMSO-broad spectrum) 1.26 (3H, t, indole N—CH$_2$—CH$_3$), 1.45 (4H, m, 2×—CH$_2$—), 1.67 (14H, 2×indole CMe$_2$ and —CH$_2$—), 3.38 (2H, —CH$_2$—OH), 4.09 (4H, 2×indole N—CH$_2$—), 4.39 (1H, —OH), 5.77+5.80 (each 1H, s, 2×methine —CH=), 7.16 (1H, m)+7.24 (1H, d)+7.33 (2H, m)=4×indole aryl-H, 7.51 (1H, d)+7.59 (1H, d)+7.66 (1H, s)=3×sulphonated indole aryl-H.

Phosphitylation to give phosphoramidite dye (11c)

The hydroxy dye (11b) (250 mg) was dissolved in dry N,N-dimethylformamide (5 ml). To the resulting solution was added N,N-diisopropylethylamine (0.17 ml) and 2-cyanoethyl-N,N-diisopropylchlorophosphoramidite, in 0.05 ml aliquots with t.l.c. monitoring (C-18 silica; ethanol 50%:water 50%. (11b), R$_f$=0.4→(11c), R$_f$=0.5). After addition of three aliquots (0.15 ml total) the reaction appeared complete. This solution was then used directly on an automated DNA synthesiser.

Synthesis of dye phosphoramidite (11f)

2-(1-Ethyl-3,3-dimethyl-2-indolinylidenemethyl)-4-(1-(5-acetoxypentyl)-3,3-dimethyl-2-indolinylidenemethyl)-cyclobutenediylium-1,3-diolate Intermediate (1m) (415 mg, 1.0 mmol) and 3-butoxy-4-(1-ethyl-3,3-dimethyl-2-indolinylidenemethyl)-cyclobut-3-en-1,2-dione (7b) (339 mg, 1.0 mmol) were mixed with anhydrous 1-butanol (10 ml); the resulting mixture was then heated at reflux for 16 h, giving a deep blue solution. The solvent was removed under reduced pressure and the residue purified by flash chromatography (silica; 4–10% methanol/dichloromethane) to give the title dye (11d), 420 mg.

$\lambda_{max}$ (MeOH) 628 nm $\delta_H$ (300 MHz, CDCl$_3$) 1.38 (3H, t, J 7.1 Hz, indole N—CH$_2$—CH$_3$), 1.47 (2H, m, —CH$_2$—), 1.65–1.85 (16H, m, 2×indole CMe$_2$ and 2×—CH$_2$—), 2.02 (3H, s, CH$_3$—COO—), 4.00 (4H, broad, 2×indole N—CH$_2$—), 4.04 (2H, t, J 6.4 Hz, —CH$_2$—OAc), 5.92–5.94 (each 1H, s, 2×methine —CH=), 6.96 (2H, m)+7.13 (2H, m)+7.30 (4H, m)=8×indole aryl-H.

2-(1-Ethyl-3,3-dimethyl-2-indolinylidenemethyl)-4-(1-(5-hydroxypentyl)-3,3-dimethyl-2-indolinylidenemethyl)-cyclobutenediylium-1,3-diolate To a solution of acetate-protected dye (11d) (400 mg) in methanol (20 ml) was added potassium carbonate (200 mg). The mixture was stirred at room temperature with t.l.c. monitoring (silica; 10% methanol/dichloromethane. (11d), R$_f$=0.6→(11e), R$_f$=0.35). After 2 h the solvent was removed under reduced pressure and the residue was purified by flash chromatography (silica; 4–10% methanol/dichloromethane) to give the title compound (11e), 338 mg.

$\lambda_{max}$ (MeOH) 628 nm $\delta_H$ (300 MHz, CDCl$_3$) 1.37 (3H, t, J 7.2 Hz, indole N—CH$_2$—CH$_3$), 1 .54 (2H, m, —CH$_2$—), 1.67–1.88 (16H, m, 2×indole CMe$_2$ and 2×—CH$_2$—), 2.45 (1H, broad s, —OH), 3.67 (2H, t, J 6.2 Hz, —CH$_2$—OH), 4.04 (4H, broad, 2×indole N—CH$_2$—), 5.92+5.98 (each 1H, s, 2×methine —CH=), 6.97 (2H, m)+7.12 (2H, m)+7.30 (4H, m)=8× indole aryl-H.

Phosphitylation to give phosphoramidite dye (11f)

The hydroxy derivatised dye (11e) (205 mg, 0.5 mmol) was dissolved in dry dichloromethane (5 ml) under nitrogen atmosphere. To the blue solution was added N,N-diisopropylethylamine (0.1 ml), followed by 2-cyanoethyl-N,N-diisopropylchlorophosphoramidite (5 drops), and the mixture stirred at room temperature for 1.5 h. T.l.c. (silica; 10% methanol/dichloromethane. (11e), R$_f$=0.35→(11f), R$_f$=0.55). The mixture was then diluted with 10% triethylamine/ethyl acetate and washed with 10% aqueous sodium carbonate solution and brine. The organic solution was dried (MgSO$_4$), filtered and the solvent removed under reduced pressure. The resulting gum was purified through a short silica plug (5–15% triethylamine/dichloromethane) to give the title compound (11f) (150 mg), after removal of solvent. This solution was then used directly on an automated DNA synthesiser.

Synthesis of phosphoramidite dye (11l)

2-4-Bis-(1-(5-hydroxypentyl)-3,3-dimethyl-2-indolinylidenemethyl)-cyclobutenediylium-1,3-diolate (11g)

Intermediate (1m) (4.35 g, 10.5 mmol) and 3,4-dihydroxycyclobut-3-en-1,2-dione (570 mg, 5.0 mmol) were mixed in dry 1-butanol (20 ml); the resulting mixture was heated at reflux for 16 h, giving a deep blue solution. T.l.c. analysis showed three blue products (silica; 15% methanol/dichloromethane. R$_f$=0.8, 0.65 and 0.55). The solvent was removed under reduced pressure and the residue dissolved in methanol (20 ml), then potassium carbonate (500 mg) added. This mixture was stirred at room temperature for 2 h; (silica; 15% methanol/dichloromethane. R$_f$=0.8, 0.65 and 0.55→R$_f$ 0.55 only). After removal of solvent the residue was partitioned between water and dichloromethane; the organic layer was retained, washed with water and brine, then dried (Na$_2$SO$_4$), filtered and the solvent removed under reduced pressure. The crude dye was purified by flash chromatography (silica; 4–15% methanol/dichloromethane) to give the title compound (11g), 1.47 g.

$\lambda_{max}$ (MeOH) 630 nm $\delta_H$ (300 MHz, CDCl$_3$) 1.52 (4H, m, 2×—CH$_2$—), 1.65–1.90 (20H, m, 2×indole CMe$_2$ and 4×—CH$_2$—), 2.7 (2H, broad, 2×—OH), 3.66 (4H, t, J 6.2 Hz, 2×—CH$_2$—OH), 4.02 (4H, broad, 2×indole N—CH$_2$—), 5.96 (2H, s,2×methine —CH=), 6.97 (2H, d, J 7.7 Hz)+7.12 (2H, t, J 7.3 Hz)+7.30 (4H, m)=8×indole aryl-H.

2-(5-Hydroxypentyl-3,3-dimethyl-2-indolinylidenemethyl)-4-(1-((4,4'-dimethoxytrityloxy)pentyl)-3,3-dimethyl-2-indolinylidenemethyl)-cyclobutenediylium-13-diolate (11h)

The bis-hydroxy dye (11g) (1.14 g, 2.0 mmol) and 4,4'-dimethoxytrityl chloride ) 0.75 g, 2.2 mmol) were dissolved in dry pyridine (10 ml) and stirred at room temperature for 16 h under nitrogen atmosphere. T.l.c. analysis (silica; 10% methanol/dichloromethane) showed three blue spots, corresponding to unreacted (11g) ($R_f$=25), product (11h) ($R_f$=0.45) and some bis-protected compound ($R_f$=0.9). The reaction was quenched by the addition of methanol (1 ml) followed by 5 mins stirring, before the solvent was removed under reduced pressure. The blue components were then separated by flash chromatography (silica; 1–10% methanol/chloroform). Fractions containing the bis-protected compound were combined and treated with trichloroacetic acid (0.5 g) for 1 hr, then combined With those containing unreacted dye. (11g) was then recovered and re-reacted as above. After reaction and work-up, the product (11h) was combined with that from the first reaction to give a total of 1.18 g.

$\lambda_{max}$ (CH$_2$Cl$_2$) 634 nm. Addition of trichloroacetic acid gave extra peaks at 416 nm and 504 nm, corresponding to DMT cation.

$\delta_H$ (300 MHz, CDCl$_3$) 1.02 (4H, m, 2×—CH$_2$—), 1.51–1.88 (20H, m, 2×indole CMe$_2$ and 4×—CH$_2$—), 2.4 (1H, broad, —OH), 3.03 (2H, t, J 6.0 Hz, —CH$_2$—ODMT), 3.66 (2H, t, J 6.2 Hz, —CH$_2$—OH), 3.76 (6H, s, 2×Ar—OMe), 4.00 (4H, broad, 2×indole N—CH$_2$—), 5.92+5.98 (each 1H, s, 2×methine —CH=), 6.78 (4H, m), 6.94 (2H, m), 7.09–7.40 (15H, m).

Phosphitylation to give phosphoramidite dye (11i)

Dye (11h) (220 mg, 0.25 mmol) was dissolved in dry tetrahydrofuran (2 ml); to this deep-blue solution was added N,N-diisopropylethylamine (0.1 ml), followed by 2-cyanoethyl-N,N-diisopropylchlorophosphoramidite (0.1 ml, 0.4 mmol). The resulting mixture was stirred at room temperature and the reaction monitored by t.l.c. (silica; ethyl acetate 50%:acetonitrile 50%. (11h), $R_f$=0.35→(11i), $R_f$=0.65). After 2 h the mixture was diluted with ethyl acetate (25 ml), washed with 5% aqueous sodium hydrogen carbonate solution and brine, then dried (MgSO$_4$) and filtered through a 0.5 cm-thick plug of silica, washing through with ethyl acetate. The solvent was removed under reduced pressure, then re-evaporated from dry toluene solution. The residue was then dried under high vacuum, re-analyzed by t.l.c. (silica; ethyl acetate 50%:acetonitrile 50%. One blue spot, $R_f$=0.65) and used directly for DNA labelling on an automated DNA synthesiser.

Synthesis of dye phosphoramidite (11l)
2-4-Bis-(1-(5-hydroxypentyl)-3,3-dimethyl-2-benzindolinylidenemethyl)-cyclobutenediylium-1,3-diolate (11j)

Synthesised by an analogous method to dye (11g), 2.96 g (43%).

$\lambda_{max}$ (MeOH) 663 nm $\delta_H$ (300 MHz, CDCl$_3$) 1.50 (4H, m, 2×—CH$_2$—), 1.66 (4H, m, 2×—CH$_2$—), 1.86 (4H, m, 2×—CH$_2$—), 1.97 (12H, s, 2×indole CMe$_2$), 3.4 (2H, s, 2×—OH), 3.62 (4H, t, 2×—CH$_2$—OH), 4.07 (4H, broad, 2×indole N—CH$_2$—), 5.97 (2H, s, 2×methine —CH=), 7.22 (2H, d), 7.32 (2H, app t), 7.47 (2H, td), 7.79 (4H, app t), 8.10 (2H, d).
2-(5-Hydroxypentyl-3,3-dimethyl-2-benzindolinylidenemethyl)-4-(1-((4,4'-dimethoxytrityloxy)pentyl)-3,3-dimethyl-2-benzindolinylidenemethyl)-cyclobutenediylium-1,3-diolate (11k)

Synthesised by an analogous method to dye (11h), 1.58 g (38%).

$\lambda_{max}$ (MeOH) 663 nm
MS (MALDI-TOF): 939

$\delta_H$ (300 MHz, CDCl$_3$) 1.4–1.9 (12H, m, 6×—CH$_2$—), 1.982+1.985 (each 6H, s, 2×indole CMe$_2$), 2.98 (2H, t, —CH$_2$—ODMT), 3.63 (2H, t, —CH$_2$—OH), 3.67 (3H, s, MMT—OMe), 4.04 (4H, broad, 2×indole N—CH$_2$—), 5.93+5.99 (each 1H, s, 2×methine —CH=), 6.69 (2H, m), 7.1–7.24 (10H, m), 7.28–7.36 (6H, m), 7.45–7.53 (2H, m), 7.70–7.83 (4H, m), 8.08–8.16 (2H, m).

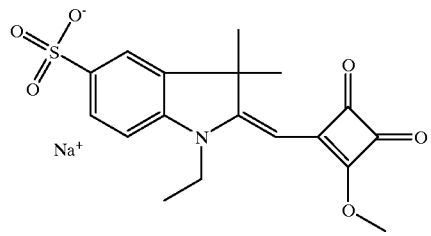

(11a)

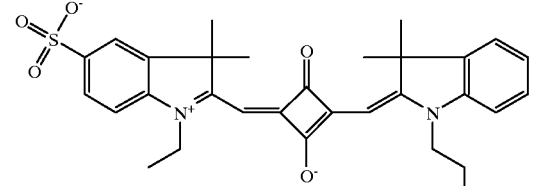

(11b) R=H
(11c) R=P(OCH$_2$CH$_2$CN)N$^i$Pr$_2$

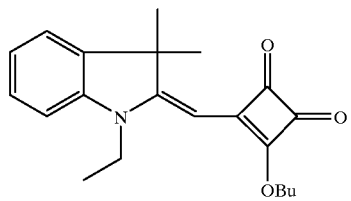

(7b)

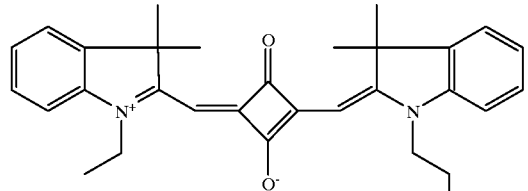

(11d) R=OAc
(11e) R=H
(11f) R=P(OCH$_2$CH$_2$CH)N$^i$Pr$_2$

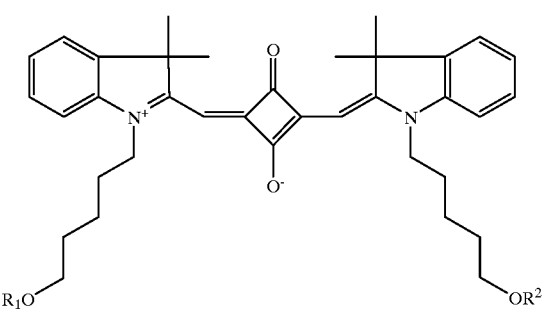

(11g) R$_1$=R$_2$=H
(11h) R$_1$=H R$_2$=ODMT
(11i) R$_1$=P(OCH$_2$CH$_2$CN)N$^i$Pr$_2$ R$_2$=ODMT

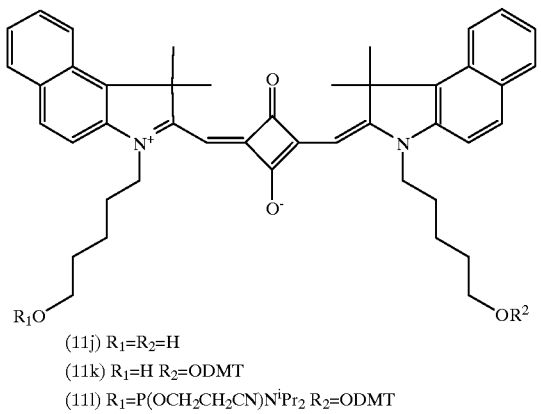

(11j) R₁=R₂=H
(11k) R₁=H R₂=ODMT
(11l) R₁=P(OCH₂CH₂CN)N$^i$Pr₂ R₂=ODMT

Incorporation of dye monomers into DNA primers and use in sequencing

Dye primers were synthesised as follows on an ABI 394 4-column DNA synthesiser using Pharmacia "Pac" base amidites [Example (11f)] or Glen Research "Ultra-Mild" amidites [(11c), (11i)]. All other synthesis reagents were from ABI. Oligonucleotides were prepared on a 0.2 μmol scale using the standard cycle except for the dye-amidite coupling reaction where the coupling time was manually extended.

The primer sequence used was a −21 M13 universal 18 mer 5' tgtaaaacgacggccagt 3'. The dye phosphoramidites were added to the 5' terminus. Cleavage from the support and subsequent deprotections were performed using either 30% NH₄OH at 60° C. for 20 min (11f)) or 0.05 M K₂CO₃ in MeOH for 2 h at 25° C. After deprotection the crude oligonucleotides were concentrated under vacuum and then precipitated by addition of ¹⁄₁₀$^{th}$ volume of 3M sodium acetate and 3 volumes of absolute ethanol. After centrifugation at 13000 g for minutes the DNA pellets were washed with 70% ethanol and dissolved in 100 μl of 95% TE buffer/5% acetonitrile ready for HPLC. A fraction was used for spectrophotomeric analysis—an approximation of percentage labelling was estimated from the ratio of the DNA to dye extinction coefficients. Final purification of the oligonucleotides was performed by HPLC using Spherisorb ODS2 C18 column [5μ] and 0.1M ammonium acetate and acetonitrile as eluent with a 5–70% acetonitrile gradient at 1 ml/min. Detection was performed at 260 and 640 nm with collection of fractions absorbing at both wavelengths. These were concentrated under vacuum and ethanol precipitated as above. The DNA pellets were dissolved in TE buffer and the OD 215–750 nm spectrum determined. Primers were diluted to 2 pmol/μl for DNA sequencing.

Sequencing experiments were performed as outlined in Example 5 with excellent results.

EXAMPLE 12

Synthesis of hydroxy squarate dye derivatives suitable for conversion to phosphoramidites.

2-(1-(13-Hydroxy-7-aza-6-oxotridecanyl)-3,3-dimethyl-5-sulphonato-2-indolinylidenemethyl)-4-(1-ethyl-3,3-dimethyl-5-sulphonato-2-indolinylidenemethyl)-cyclobutenediylium-1,3-diolate (12a)

Activation of dye (2b) as the NHS ester

Dye (2b) (100 mg, 0.11 mmol), O-(N-succinimidyl)-N,N,N',N'-bis(tetramethylene) uronium hexafluorophosphate (70 mg, 0.17 mmol) and N,N-diisopropylethylamine (10 drops) were mixed in dry N,N-dimethylformamide (2 ml) to give a deep blue solution. The reaction to give the dye-NHS ester was monitored by t.l.c. (C-18 silica; methanol 40%:water 60%. (2b) R$_f$=0.2, NHS ester R$_f$=0.3). The reaction was complete after 2 h. The product was used in the next reaction without any further manipulations.

2-(1-(13-Hydroxy-7-aza-6-oxotridecanyl)-3,3-dimethyl-5-sulphonato-2-indolinylidenemethyl)-4-(1-ethyl-3,3-dimethyl-5-sulphonato-2-indolinylidenemethyl)-cyclobutenediylium-1,3-diolate (12a)

To the above mixture was added 6-aminohexan-1-ol (25 mg, 0.2 mmol) and the mixture stirred at room temperature with t.l.c. monitoring (C-18 silica; methanol 50%:water 50%. NHS ester R$_f$=0.4, (12a) R$_f$=0.55). Reaction was complete after 1 h. The crude dye was precipitated with diethyl ether, dried under vacuum, then purified by prep. HPLC (C-18 silica column; water→methanol gradient). Yield of the titled compound (12a)=70 mg.

2-(1-(14-(4,4'-Dimethoxytrityloxy)-13-hydroxy-11-oxa-7-aza-6-oxotetradecanyl)-3,3-dimethyl-5-sulphonato-2-indolinylidenemethyl)-4-(1-ethyl 3,3-dimethyl-5-sulphonato-2-indolinylidenemethyl)-cyclobutenediylium-1,3-diolate (12b)

Activation of dye (2b) as the NHS ester

Dye (2b) (40 mg, 0.05 mmol) was reacted as described in Example (12a), to give the NHS ester which was used without purifying.

2-(1-(14-(4,4'-Dimethoxytrityloxy)-13-hydroxy-11-oxa-7-aza-6-oxotetradecanyl)-3,3-dimethyl-5-sulphonato-2-indolinylidenemethyl)-4-(1-ethyl-3,3-dimethyl-5-sulphonato-2-indolinylidenemethyl)-cyclobutenediylium-1,3-diolate (12b)

To the above mixture was added the 7-(4,4'-dimethoxytrityloxy)-6-hydroxy-4-oxaheptylamine (30 mg, 0.067 mmol) and stirring continued. The reaction was monitored by t.l.c. (C-18 silica; ethanol 50%:water 50%. NHS ester R$_f$=0.8, (12b) R$_f$=0.6). After 1 h the reaction was complete and the dye was precipitated by adding diethyl ether. The crude product was purified by prep. t.l.c. (C-18 silica; methanol 60%:water 40%) to give pure dye (12b), 55 mg.

$\lambda_{max}$ (MeOH) 636 nm; $\lambda_{em}$ (MeOH)

$\delta_H$ (300 MHz, DMSO) 1.1–1.35 (5H, m), 1.4–1.7 (18H, m, indole CMe₂ and 3×—C$\underline{H}_2$—), 1.97 (2H, t, R—C$\underline{H}_2$—CONH—), 2.85 (2H, m, glycol —C$\underline{H}_2$—), 2.94 (2H, m, glycol —C$\underline{H}_2$—), 3.10 (1H, m, glycol —C$\underline{H}$—), 3.28 (4H, m, —CONH—C$\underline{H}_2$— and —C$\underline{H}_2$O-glycol), 3.64 (6H, s, 2×Ar—OMe), 4.04 (4H, broad m, 2×indole N—C$\underline{H}_2$—), 4.81 (1H, appd, —O$\underline{H}$), 5.74 (2H, s,2×methine —C$\underline{H}$=), 6.79 (4H, m)+7.08–7.28 (9H, m)=13×DMT aryl-H, 7.32 (2H, m)+7.55 (2H, m)+7.61 (2H, m)=6×indole aryl-H, 7.69 (1H, t, —CON$\underline{H}$—).

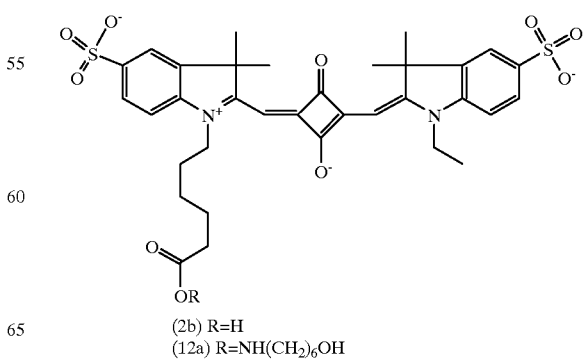

(2b) R=H
(12a) R=NH(CH₂)₆OH

-continued

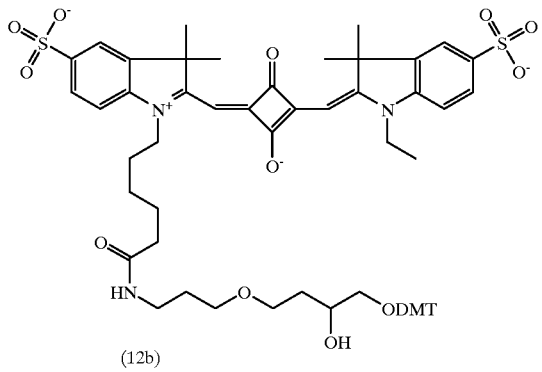

(12b)

EXAMPLE 13
Synthesis of non sulphonated squarate dyes and comparison of photostability properties with sulphonic acid derivatised squarate dyes.

2-(1-(5-Carboxypentyl)-3,3-dimethyl-2-indolinylidenemethyl)-4-(1-ethyl-3,3-dimethyl-2-indolinylidenemethyl)cyclobutenediylium-1,3-diolate (13a)

The title compound was prepared as its butyl ester in a similar manner to (2b) butyl ester, vide supra, (1i), squaric acid and (1g).

$\lambda_{max}$(MeOH) 630 nm; $\lambda_{em}$(MeOH) 643 nm $\delta_H$ (270 MHz;CDCl$_3$) 0.93 (3H, t, J 7.3), 1.3–1.92 (13H, m), 1.78 (12H, s), 2.32 (2H,t, J 7.3), 3.94.2 (4H, m), 4.06 (2H, t, J 6.7), 5.94 (1H, s), 5.97 (1H, s), 6.95–7.05 (2H, m), 7.11–7.25 (2H, m) and 7.26–7.45 (4H, m);

Saponification of the butyl ester in an analogous method to Example (2b) gave the title compound (13a)

$\delta_H$ (270 MHz;CDCl$_3$) 1.40 (3H, t, J 7.3), 1.60–2.00 (6H, m), 1.78 (12H, s), 2.42–2.50 (2H, m), 3.95–4.18 (4H, m), 5.90–6.00 (1H, brs), 6.05–6.15 (1H, brs), 6.93–7.08 (2H, m), 7.10–7.25 (2H, m) and 7.28–7.45 (4H, m)

Activation of (13a) to an succinimidyl ester was carried out as per the method described in Example (4)

2-(1-Butyl-3,3-dimethyl-5-carboxymethyl-2-indolinylidenemethyl)-4-(1-ethyl-3,3-dimethyl-2-indolinylidenemethyl)cyclobutenediylium-1,3-diolate (13b)

The title compound was prepared as its butyl ester in a similar manner to Example (2b) butyl ester, vide supra, (1j), squaric acid and (1g).

$\lambda_{max}$ (MeOH) 632 nm $\delta_H$ (270 MHz;CDCl$_3$) 0.90 (3H, t), 0.98 (3H, t), 1.20–2.10 (7H, m), 1.80 (12H, s), 3.65 (2H, br s), 3.90–4.20 (6H, m), 5.95 (2H, s), 6.85–7.05 (2H, m) and 7.15–7.45 (5H, m)

Saponification of the butyl ester in an analogous method to Example (2b) gave the title compound (13b)

$\delta_H$ (270 MHz;CDCl$_3$) 0.95 (3H, t), 1.35–1.55 (5H, m), 1.70–1.90 (14H, m), 3.70 (2H, s), 3.80–4.20 (4H, m), 5.95 and 6.00 (each 1H, s), 6.92 (1H, d), 7.00 (1H, d), 7.15 (1H, d) and 7.32–7.41 (4H, m)

Activation of (13a) to an succinimidyl ester was carried out as per the method described in Example (4)

2-(1-(5-Carboxypentyl)-3,3-dimethyl-2-benzindolinylidenemethyl)-4-(1-ethyl-3,3-dimethyl-2-benzindolinylidenemethyl)-cyclobutenediylium-1,3-diolate (13c)

A mixture of (1k) (119 mg), (1l) (162 mg) squaric acid (37 mg) and potassium acetate (98 mg) in 2-butanol (20 ml) was heated at 100° C. for 10 h and then concentrated in vacuo. Purification of the residue by HPLC (C$_{18}$ isocratic MeOH) afforded the title compound (13c).

$\delta_H$ (270 MHz;CDCl$_3$) 1.45 (3H, t), 1.76 (2H, m), 1.85–2.05 (4H, m), 2.07 (12H, s), 2.48 (2H, m), 4.10–4.28 (4H, m), 5.98 and 6.12 (each 1H, s), Activation of (13c) to an succinimidyl ester was carried out as per the method described in Example (4).

2-(1-(5-Carboxypentyl)-3,3-dimethyl-2-indolinylidenemethyl)-4-(3-ethyl-2-benzothiazolinylidenemethyl)-cyclobutenediylium-1,3-diolate (13d)

Synthesised from the intermediate half-dye, prepared from intermediate (1l) and squaric acid, and intermediate (1s) to give the n-butyl ester as per Example (2b).

Saponification gave the free acid (13d) and this was converted to the N-succinimidyl ester as per Example (4).

$\lambda_{max}$(MeOH) 638 nm $\delta_H$ (270 MHz; CDCl$_3$) 1.46 (3H, t, CH$_2$Me), 1.63–2.07 (6H, m), 1.75 (6H, s, 2×Me), 2.46 (2H, t, CH$_2$CO$_2$H), 3.95 (2H, br t, NCH$_2$CH$_2$), 4.25 (2H, q, NCH$_2$CH$_3$), 5.93 and 6.00 (each 1H, s, 2×vinyl CH), 6.90 (1H, d, ArH), 7.04–7.54 (6H, series m, ArH) and 7.61 (1H, d, ArH)

2-(1-(5-Carboxypentyl)-3,3-dimethyl-2-benzindolinylidenemethyl)-4-(1-methyl-3,3-dimethyl-2-indolinylidenemethyl)-cyclobutenediylium-1,3-diolate (13e)

Synthesised from the intermediate half-dye, prepared from 1,2,3,3-tetramethylindoleninium iodide and squaric acid, and intermediate (1l) to give the n-butyl ester as per Example (2b). Saponification gave the free acid (13e)

$\lambda_{max}$(MeOH) 644 nm

Free acid: $\delta_H$ (300 MHz; CDCl$_3$) 1.70–1.80 (12H, m, indole CMe$_2$+3×CH$_2$), 2.05 (6H, s, benzindole CMe$_2$), 2.47 (2H, br t, CH$_2$CO$_2$H), 3.57 (3H, brs, indole NCH$_3$), 4.16 (2H, brt, benzindole NCH$_2$—), 5.88+6.14 (each 1H, s, vinylH), 7.00 (1H, d), 7.13 (1H, m), 7.26–7.36 (3H, m), 7.43 (1H, app t), 7.58 (1H, app t), 7.89 (2H, app t), 8.20 (1H, d).

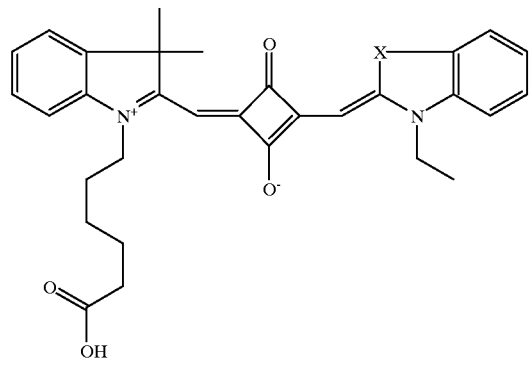

(13a) X=CMe$_2$
(13d) X=S

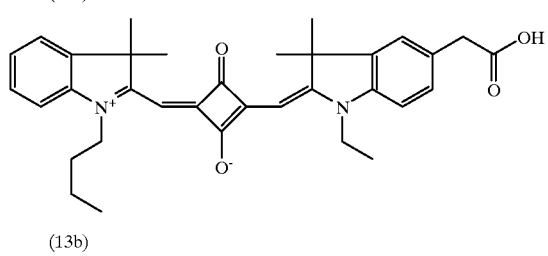

(13b)

-continued

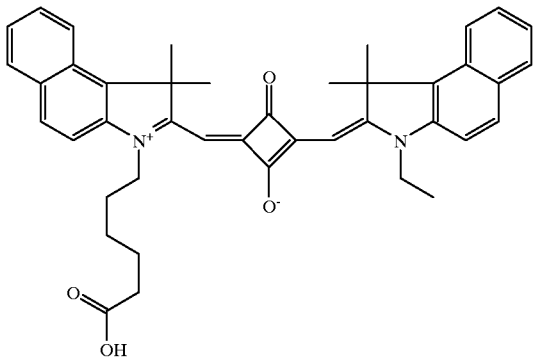

(13c)

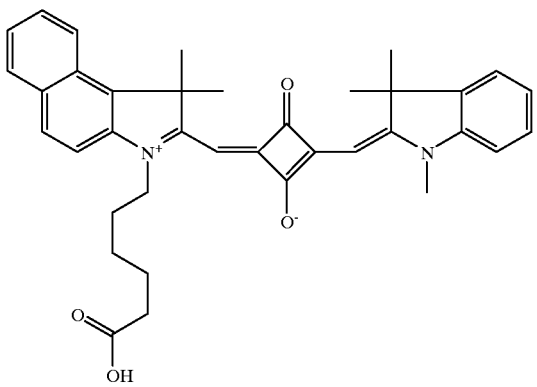

(13e)

| EXAMPLE | OVERALL CHARGE | NO. OF ARYL SULPHONATE GROUPS | NO. OF ALKYL SULPHONATE GROUPS | $T_{1/2}$ (MIN) |
|---|---|---|---|---|
| Photostability of Indolinium Based Squarate Dyes | | | | |
| Cy5 ™ | −1 | 2 | 0 | 26.4 |
| 13a | 0 | 0 | 0 | 25.4 |
| 13b | 0 | 0 | 0 | 26.1 |
| 2f | −1 | 1 | 0 | 40.4 |
| 2d | −1 | 1 | 0 | 51.0 |
| 2e | −3 | 1 | 2 | 61.2 |
| 2c | −2 | 2 | 0 | 81.3 |
| 2a | −3 | 2 | 1 | 88.5 |
| 2b | −2 | 2 | 0 | 94.9 |
| Benzindole Based Dyes | | | | |
| 13c | 0 | 0 | 0 | 22.4 |
| 2h | −2 | 2 | 0 | 38.9 |
| Photostability of Mixed Thiazolinium/Indolinium Based Squarate Dyes | | | | |
| 13d | 0 | 0 | 0 | 7.7 |
| 3b | −1 | 0 | 1 | 10.7 |
| 3a | −1 | 1 | 0 | 15.2 |

EXAMPLE 14
Synthesis of an Energy Transfer Cassette
2,4-bis(1-(5-Carboxypentyl)-3,3-dimethyl-5-sulphonato-2-indolinylidenemethyl)cyclobutenediylium-1,3-diolate (14a)

Intermediate (1c) (1.42 g, 3.0 mmol) and squaric acid (0.17 g, 1.5 mmol) were mixed in anhydrous 1-butanol (10 ml). The resulting mixture was heated at 110° C. for 65 h. A deep green-blue colour was generated during this time, with some dark solid present. The solvent was removed under reduced pressure; the residue was then redissolved in methanol (15 ml), and a solution of potassium hydroxide (0.5 g, 9.0 mmol) in water (10 ml) added. This solution was stirred for 20 h. T.l.c. analysis (C18-silica; methanol 50%:water 50%. Major blue spot at $R_f$=0.6). The solution was then neutralised with acetic acid before purification by prep. HPLC (C18, water→methanol gradient) to give title dye (14a).

$\lambda_{max}$ (MeOH)=638 nm; $\lambda_{ex}$ (MeOH)=636 nm; $\lambda_{em}$=644 nm.

$\delta_H$ (300 MHz, $CD_3OD$) 1.52 (4H, m), 1.70 (4H, m), 1.77 (12H, s, indole $CMe_2$), 1.86 (4H, m), 2.35 (4H, t, J 7.3, 2×—$CH_2CO_2H$), 4.17 (4H, broad s, 2×indole N—$CH_2$—), 6.03 (2H, s, 2×vinyl —C$\underline{H}$=), 7.33 (2H, d, J 7.7 Hz), 7.86–7.90 (4H, m).

3-(3-(t-Butyloxycarbonylamino)propylamino)-2,4-bis(3-ethyl-2-benzothiazolinylidenemethyl)-cyclobutenediylium-1-olate methosulphate (14b)

Dye (9b) (560 mg, 1.0 mmol) was dissolved in dichloromethane (20 ml). To the resulting deep blue solution was added t-butyl-N-(3-aminopropyl) carbamate (190 mg, 1.1 mmol). This mixture was stirred at room temperature until the reaction was complete by t.l.c. (silica; 10% methanol in dichloromethane. (9b) $R_f$=0.2→(14b) $R_f$=0.3). The solution was then washed with water, dried ($Na_2SO_4$), filtered and the solvent removed under reduced pressure to a volume of about 5 ml. The product was then precipitated by addition of diethyl ether; the resulting solid was collected, washed with ether and dried under vacuum at 35° C. to give the title dye (14b) (640 mg).

$\lambda_{max}$ (MeOH) 658 nm; $\lambda_{ex}$ (MeOH) 658 nm; $\lambda_{em}$=670 nm.

$\delta_H$ (300 MHz, $CDCl_3$) 1.40 (9H, s, —$CMe_3$), 1.48 (6H, t, J 7.0 Hz, thiazole N—$CH_2$—C$\underline{H}_3$), 1.97 (2H, quin, —$CH_2$—C$\underline{H}_2$—$CH_2$—), 3.31 and 3.66 (each 2H, q, NH—C$\underline{H}_2$—), 3.79 (3H, s, methosulphate), 4.13 and 4.44 (each 2H, q, thiazole N—C$\underline{H}_2$—$CH_3$), 5.69 (1H, s, vinyl—C$\underline{H}$=), 5.89 (1H, broad t, BOC—N$\underline{H}$—), 6.58 (1H, s, vinyl—C$\underline{H}$=), 7.12–7.20 (2H, m), 7.28–7.36 (3H, m), 7.42–7.47 (2H, m), 7.58 (1H, d), 8.83 (1H, broad t, squarate-N$\underline{H}$—$CH_2$—).

3-((Aminopropyl)amino)-2,4-bis(3-ethyl-2-benzothiazolinylidenemethyl)-cyclobutenediylium-1-olate trifluoroacetate, trifluoroacetic acid salt (14c)

The protected dye (14b) (250 mg) was dissolved in chloroform (4 ml). To the deep blue solution was added trifluoroacetic acid (2 ml), turning the solution a yellow-brown colour. This mixture was stirred for 1 h, the solvent was removed under reduced pressure. The residue was redissolved in 4 ml of 10% methanol/dichloromethane, restoring the blue colour. The dye was precipitated by addition of diethyl ether; the solid was collected, washed well with fresh ether and dried under vacuum at 50° C. to give the title amine dye (14c), 245 mg.

$\lambda_{max}$ (MeOH)=656 nm; $\lambda_{ex}$ (MeOH)=657 nm; $\lambda_{em}$=671 nm.

$\delta_H$ (300 MHz, DMSO) 1.27–1.36 (6H, 2×overlapping t, thiazole N—$CH_2$—C$\underline{H}$3),1.95 (2H, quin, —$CH_2$—C$\underline{H}_2$—$CH_2$—), 2.96 (2H, broad, —C$\underline{H}_2$—$NH_3^+$), 3.72 (2H, q, —NH—C$\underline{H}_2$—), 4.33–4.45 (4H, 2×overlapping broad q, thiazole N—C$\underline{H}_2$—$CH_3$), 5.91 and 6.23 (each 1H, s, vinyl—C$\underline{H}$=), 7.32–7.42 (2H, app quin.), 7.49–7.58 (2H, m), 7.65–7.75 (2H, 2×d), 7.84 (3H, broad s, —N$\underline{H}_3^+$), 7.94–8.02 (2H, 2×d), 8.98 (1H, broad t, squarate-N$\underline{H}$—$CH_2$—).

Coupling of (14a) to (14c) to give the ET cassette (14d)

Diacid dye (14a) (60 mg) was dissolved in anhydrous N,N-dimethylformamide (1 ml); to the deep blue solution was added O-(N-succinimidyl)-N,N,N',N'-bis(tetramethylene)uronium hexafluorophosphate (27 mg) and N,N-diisopropylethylamine (50 μl). This mixture was stirred at room temperature for 1 h. T.l.c. (C18 silica; methanol 50%:water 50%. (14a) $R_f$=0.5→mono-NHS ester, $R_f$=0.35 and bis-NHS ester, $R_f$=0.2). To the above mixture was then added N,N-diisopropylethylamine (150 μl) and amine dye (14c) (45 mg); this mixture was stirred for another 2 h. T.l.c. (C18 silica; methanol 85%:water 15%. (14a) $R_f$=0.95, amine (14c) $R_f$=0.1, product (14d) $R_f$=0.55). The crude dye was isolated by precipitation with diethyl ether. The crude solid was purified by prep. HPLC (C18 silica; water→methanol gradient) to give the compound dye (14d).

$\lambda_{max}$ (MeOH)=638 nm with shoulders to short and long wavelengths.

$\lambda_{ex}$ (MeOH)=640 nm; $\lambda_{em}$=671 nm.

$\delta_H$ (300 MHz, DMSO) 1.17–1.35 (8H, m, 2×thiazole N—CH$_2$—C$\underline{H}_3$ and —C$\underline{H}_2$—), 1.50–1.72 (24H, m, 2×indole N—CH$_2$—C$\underline{H}_3$ and 6×—C$\underline{H}_2$—), 2.03 (2H, broad t, —C$\underline{H}_2$—CONH), 2.18 (2H, t, 7.2 Hz, —C$\underline{H}_2$—CO$_2$H), 3.07 and 3.52 (each 2H, broad, NH—C$\underline{H}_2$—), 4.04 (4H, broad, 2×indole N—C$\underline{H}_2$—CH$_3$), 4.38 (4H, broad, 2×thiazole N—C$\underline{H}_2$—CH$_3$), 5.77 (2H, s, indole vinyl-H), 5.85 and 6.31 (each 1H, s, thiazole vinyl-H), 7.21–7.39 (4H, m, 4×aryl-H), 7.43–7.72 (8H, m, 8×aryl-H), 7.87–7.99 (3H, m, 2×aryl-H and —CON$\underline{H}$—), 8.82 (1H, broad t, squarate —N$\underline{H}$—CH$_2$—).

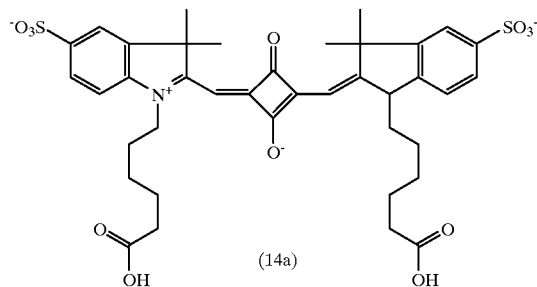

(14a)

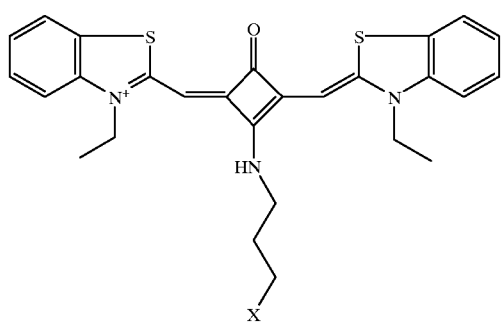

(14b) R=NH—CO·OC(CH$_3$)$_3$
(14c) R=NH$_3^+$ CF$_3$CO$_2^-$

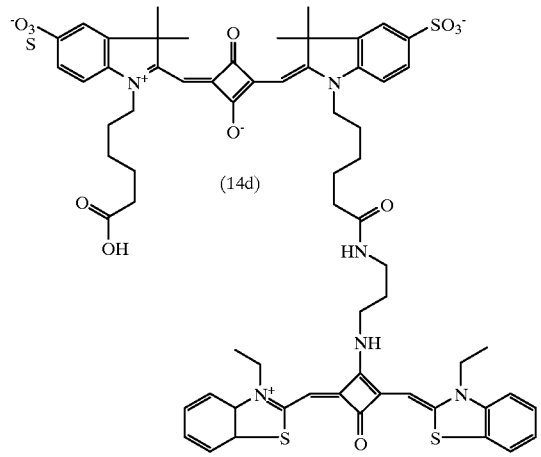

(14d)

EXAMPLE 15
Synthesis of a Squarate Dye Labelled Peptides Using Both Solution and Solid Phase Approaches
Representative example:

SYNTHESIS OF PEPTIDE ON SOLID PHASE

The serine protein kinase substrate peptide (NH$_2$—ARRVRSAARRS—OH) was synthesised using solid phase Fmoc chemistry, the N-terminal Fmoc group was removed at the end of the synthesis. The peptide was cleaved from 100 mgs of resin and deprotected using a mixture of trifluoroacetic acid, water, thioanisole and ethanedithiol (95:2.5:5:2.5 v/v, 2 ml) for 90 minutes. The crude peptide was precipitated from cold diethyl ether, centrifuged down, dried in vacuo, then after dissolving in water, purified by semi-preparative HPLC using a Vydac C-18 reverse phase column at a flow rate of 4 ml/minute and a gradient of water/0.1% TFA to 60% acetonitrile/0.1% TFA over a period of 30 minutes. Detection was at 230 nm. A major peak eluting at 8.5 minutes was collected and freeze dried to give 10 mg of the desired peptide as a white solid.

PREPARATION OF DYE-NHS ESTER

Squarate dye (2i) (88 mg, 0.117 mmol), N-hydroxysuccinimide (20 mg, 0.174 mmol) and N-cyclohexyl-N'-(2-morpholinoethyl)-carbodiimide methyl-p-toluenesulphonate (45 mg, 0.11 mmol) and a single small crystal of 4-dimethlylaminopyridine were placed in a round bottomed flask fitted with a magnetic stirrer bar and dry DMF (2 ml) was added. The mixture was stirred for 16 hours at ambient temperature, then the solvent was removed under vacuum and the blue residue was dissolved in dry DMSO (1 ml).

SOLID PHASE LABELLING 100 mg of peptide resin (equivalent to ~0.03 mmol of peptide) was weighed into a 1.5 ml polypropylene V-vial then 0.4 ml of the dye-NHS ester solution was added followed by 0.6 ml of dry DMSO plus 0.02 ml diisopropylethylamine. The vial was placed on rollers in the dark at ambient temperature for 18 hrs. The resin was filtered off, washed with 2×1 ml DMSO, 2×1 ml methanol and finally 2×1 ml dichloromethane, then dried in vacuo. The resin was treated with 2 ml of the deprotection mixture as outlined above to cleave the labelled peptide from the resin and remove the protecting groups. The peptide was precipitated from diethyl ether as a blue solid. This was treated in the same way as the unlabelled peptide described above. Upon HPLC purification, a blue coloured peak eluted after 22.5 minutes, this was collected and freeze dried to give 3 mg of blue solid. Mass spec gave a peak at 1933 m.u. (calculated mol. wt. of the squarate dye labelled peptide=1930).

SOLUTION PHASE LABELLING 0.3 ml of the dye-NHS solution was added to 5.0 mg (0.004 mmol) of the peptide in a polypropylene V-vial, a further 0.7 ml of dry DMSO plus 0.02 ml of diisopropyl-ethylamine was added, then the vial was placed on rollers in the dark for 18 hours. The mixture was then separated on semi-prep HPLC using the same conditions as outlined above

What is claimed is:

1. A squarate dye of the formula (I) or (II) or (IIa)

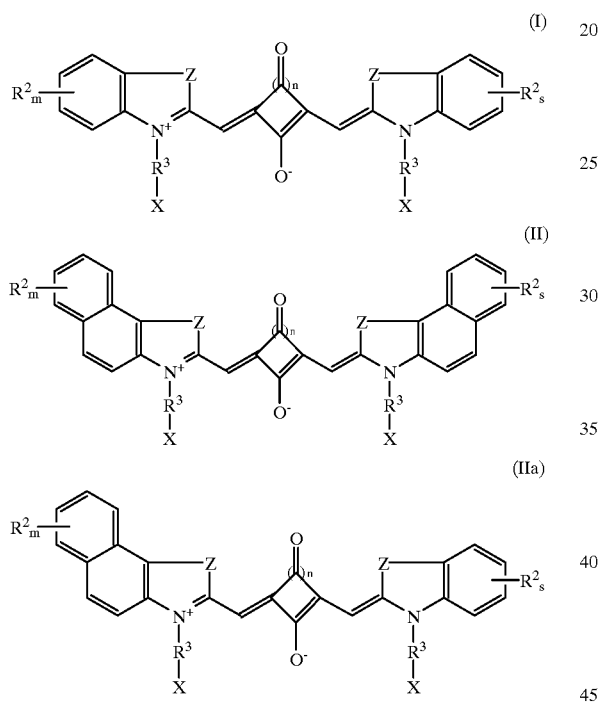

where
each Z is independently O or S or $CR^1_2$,
n=1–3,
each of s and m is 0, 1 or 2,
$R^1$ is lower alkyl (1–4 carbon chain),
each $R^2$ is independently selected from electron donating and electron withdrawing groups or is a branched or straight chain of up to 30 carbon atoms incorporating one to five positively charged nitrogen atoms,
each $R^3$ is independently selected from: alkylene, alkenylene and alkynylene (1–20 carbon chain), or is a branched or straight chain of up to 30 carbon atoms incorporating one to five ether oxygen atoms or arylene rings or positively charged nitrogen atoms,
at least one X is a nucleophilic functional group, such as OH, SH or $NH_2$, or alternatively a grouping capable of reacting with a nucleophile,
and any other X present is independently selected from H and $SO_3^-$ and the residue of a squarate dye of formula (I) or (II) or (IIa) and another fluorochrome,
provided that at least one $R^2$ is $SO_3^-$ and/or at least one X is phosphoramidite.

2. A squarate dye of the formula (III) or (IV) or (IVa)

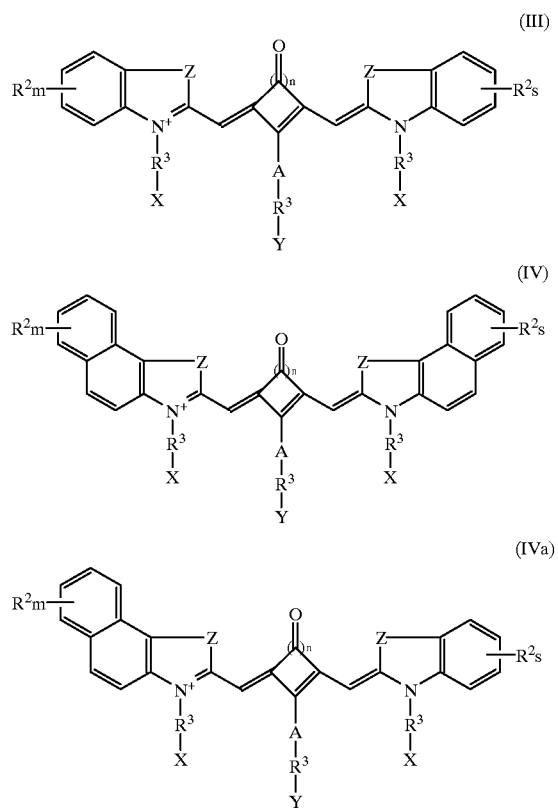

where
each Z is independently O or S or $CR^1_2$,
n=1–3,
each of s and m is 0, 1 or 2,
$R^1$ is lower alkyl (1–4 carbon chain),
each $R^2$ is independently selected from electron donating and electron withdrawing groups or is a branched or straight chain of up to 30 carbon atoms incorporating one to five positively charged nitrogen atoms,
each $R^3$ is independently selected from: alkylene, alkenylene and alkynylene (1–20 carbon chain), or is a branched or straight chain of up to 30 carbon atoms incorporating one to five ether oxygen atoms or arylene rings or positively charged nitrogen atoms,
at least one X is a nucleophilic functional group, such as OH, SH or $NH_2$, or alternatively a grouping capable of reacting with a nucleophile
and any other X present is independently selected from H and $SO_3^-$ and the residue of a squarate dye of formula (III), (IV) or (IVa) and another fluorochrome,
A is O, $NR^4$ or S,
$R^4$ is alkyl, alkenyl, alkynyl or H, and
each Y is independently X or H,
provided that at least one $R^2$ is $SO_3^-$ and/or at least one X is phosphoramidite.

3. A squarate dye according to claim 1 or claim 2, wherein at least one $R^2$ is $SO_3^-$.

4. A squarate dye according to claim 1 or claim 2, wherein n is 1 and Z is —$C(CH_3)_2$.

5. A squarate dye according to claim 1 or claim 2, wherein 1 to 5 $SO_3^-$ groups are present.

6. A squarate dye according to claim 1 or claim 2, wherein at least one X is selected from $CO_2H$, activated carboxyl, CO active ester, NCS, O phosphoramidite, $NCOCH_2I$ and

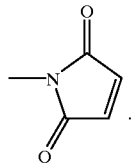

7. A squarate dye according to claim 1 or claim 2, wherein each $R^2$ is individually selected from halogen, alkoxy, primary secondary and tertiary amine, nitro, $SO_3^-$ and —$R^3X$.

8. An adduct of a biological molecule with a squarate dye according to claim 1 or claim 2.

9. An adduct of a nucleoside or nucleotide or analogue or oligonucleotide or nucleic acid with a squarate dye of the formula (I) or (II) or (IIa) or (III) or (IV) or (IVa)

where each Z is independently O or S or $CR^1_2$, n=1–3, $R^1$ is lower alkyl (1–4 carbon chain), each $R^2$ is independently selected from electron donating and electron withdrawing groups such as halogen, alkoxy, primary secondary and tertiary amino, nitro, $SO_3^-$, and —$R^3$—X, or is a branched or straight chain of up to 30 carbon atoms incorporating one to five positively charged nitrogen atoms, each $R^3$ is independently selected from: alkylene, alkenylene and alkynylene (1–20 carbon chain), or is a branched or straight chain of up to 30 carbon atoms incorporating one to five ether oxygen atoms or arylene rings or positively charged nitrogen atoms, at least one X is a nucleophilic functional group, such as OH, SH or $NH_2$, or alternatively a grouping capable of reacting with a nucleophile, in which case X is preferably selected from the following $CO_2H$, activated carboxyl such as acid halide or anhydride, CO active ester, NCS, O phosphoramidite, $NC(O)CH_2I$ and

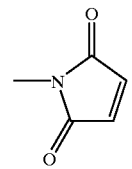

any other X present is independently selected from H and $SO_3^-$ and the residue of a squarate dye (whereby dimers and oligomers of the dyes shown as monomers of formula (I), (II), (IIa), (III), (IV) and (IVa) are envisaged), or other fluorochrome, each of s and m is 0, 1 or 2, A is O, $NR^4$ or S, $R^4$ is alkyl, alkenyl, alkynyl or H, and each Y is independently X or H.

10. An adduct as claimed in claim 9, wherein the adduct has the formula Q—N—CO—Sq, where Q is a nucleotide or nucleotide analogue or oligonucleotide residue, and Sq is a residue of a squarate dye, the two being joined by an amide linkage formed between an amine group of Q and a carboxylate group of Sq.

11. An improved fluorescent sequencing method, which comprises using an adduct according to claim 9 or claim 10.

12. A fluorescent labelling complex comprising:

a first or donor fluorochrome having first absorption and emission spectra;

a second or acceptor fluorochrome having second absorption and emission spectra, the wavelength of the emission maximum of said second fluorochrome being longer than the wavelength of the emission maximum of said first fluorochrome, and a portion of the absorption spectrum of said second fluorochrome overlapping a portion of the emission spectrum of said first fluorochrome;

at least one linker for covalently attaching said first and second fluorochromes for transfer of resonance energy transfer between said first and second fluorochromes;

a target bonding group capable of forming a covalent bond with a target compound;

wherein at least one of the said first and second fluorochromes is a squarate dye according to claim 1 or claim 2.

* * * * *